(12) United States Patent
Levner et al.

(10) Patent No.: US 11,506,652 B2
(45) Date of Patent: *Nov. 22, 2022

(54) COMPOSITIONS AND METHODS OF CELL ATTACHMENT

(71) Applicant: Emulate Inc., Boston, MA (US)

(72) Inventors: Daniel Levner, Brookline, MA (US); Kyung JIn Jang, Andover, MA (US); Jacob Fraser, Somerville, MA (US); S. Jordan Kerns, Reading, MA (US); Antonio Varone, West Roxbury, MA (US); Dongeun Huh, Philadelphia, PA (US)

(73) Assignee: EMULATE, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/648,293

(22) Filed: Jul. 12, 2017

(65) Prior Publication Data

US 2018/0024117 A1    Jan. 25, 2018

Related U.S. Application Data

(60) Provisional application No. 62/361,259, filed on Jul. 12, 2016.

(51) Int. Cl.
| | |
|---|---|
| *C12N 5/00* | (2006.01) |
| *C12N 5/02* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *G01N 33/50* | (2006.01) |
| *C07K 14/78* | (2006.01) |
| *C12N 5/071* | (2010.01) |
| *C12M 3/06* | (2006.01) |
| *C12M 1/00* | (2006.01) |
| *C12M 1/12* | (2006.01) |
| *C12N 5/077* | (2010.01) |

(52) U.S. Cl.
CPC .......... *G01N 33/5032* (2013.01); *C07K 2/00* (2013.01); *C07K 14/78* (2013.01); *C12M 23/16* (2013.01); *C12M 23/20* (2013.01); *C12M 25/02* (2013.01); *C12N 5/0018* (2013.01); *C12N 5/0068* (2013.01); *C12N 5/067* (2013.01); *C12N 5/0658* (2013.01); *G01N 33/5014* (2013.01); *C12N 2500/32* (2013.01); *C12N 2521/00* (2013.01); *C12N 2533/30* (2013.01); *C12N 2533/50* (2013.01); *C12N 2533/52* (2013.01); *C12N 2533/54* (2013.01); *C12N 2533/90* (2013.01); *C12N 2535/10* (2013.01); *C12N 2537/10* (2013.01); *G01N 33/5044* (2013.01)

(58) Field of Classification Search
None
See application file for complete search history.

(56) References Cited

U.S. PATENT DOCUMENTS

| | | | |
|---|---|---|---|
| 7,160,687 B1 | 1/2007 | Kapur et al. | 435/7.2 |
| 8,647,861 B2 | 2/2014 | Ingber et al. | 435/289.1 |
| 2003/0219713 A1 | 11/2003 | Valencia et al. | 435/7.1 |
| 2006/0103719 A1 | 5/2006 | Katzir et al. | 347/255 |
| 2006/0270032 A1* | 11/2006 | Bhatia | C12N 5/0671 435/325 |
| 2007/0166771 A1 | 7/2007 | Kapur et al. | 435/287.2 |
| 2010/0135855 A1 | 6/2010 | Pierik et al. | 422/502 |
| 2010/0215717 A1 | 8/2010 | Soker et al. | 623/5.16 |
| 2013/0023648 A1 | 1/2013 | Wnek et al. | 530/356 |
| 2017/0158997 A1* | 6/2017 | Ingber | C12M 23/16 |
| 2018/0023050 A1* | 1/2018 | Levner | C12N 5/0018 435/396 |
| 2018/0024116 A1* | 1/2018 | Levner | C12N 5/0018 514/1.1 |
| 2018/0024118 A1* | 1/2018 | Levner | C12N 5/0018 514/1.1 |

(Continued)

FOREIGN PATENT DOCUMENTS

| | | |
|---|---|---|
| WO | WO/2009/032164 | 3/1909 |
| WO | WO/2015/061907 | 5/1915 |
| WO | WO/2013/086502 | 6/2013 |

(Continued)

OTHER PUBLICATIONS

BioLamina, "General Laminin Information," available online at http://www.biolamina.com/laminin-product-questions-answers, 5 pages (2014) (Year: 2014).*

(Continued)

*Primary Examiner* — Thea D'Ambrosio
(74) *Attorney, Agent, or Firm* — Medlen & Carroll, LLP

(57) ABSTRACT

Compositions, devices and methods are described for improving adhesion, attachment, and/or differentiation of cells in a microfluidic device or chip. In one embodiment, one or more ECM proteins are covalently coupled to the surface of a microchannel of a microfluidic device. The microfluidic devices can be stored or used immediately for culture and/or support of living cells such as mammalian cells, and/or for simulating a function of a tissue, e.g., a liver tissue, muscle tissue, etc. Extended adhesion and viability with sustained function over time is observed.

7 Claims, 26 Drawing Sheets

(3 of 26 Drawing Sheet(s) Filed in Color)

(56) References Cited

U.S. PATENT DOCUMENTS

| | | | | |
|---|---|---|---|---|
| 2018/0024119 A1* | 1/2018 | Levner | ............... | C12N 5/0018 514/1.1 |
| 2018/0024120 A1* | 1/2018 | Levner | ............... | C12N 5/0018 514/1.1 |

FOREIGN PATENT DOCUMENTS

| | | |
|---|---|---|
| WO | WO/2015/138032 | 9/2015 |
| WO | WO/2015/138034 | 9/2015 |
| WO | WO/2016/004394 | 1/2016 |

OTHER PUBLICATIONS

Cosmos, "Ultraviolet," available online at http://astronomy.swin.edu.au/cosmos/U/Ultraviolet, 2 pages (accessed on Sep. 23, 2018) (Year: 2018).*

ThermoFisher Scientific, "Chemistry of Crosslinking," available online at https://www.thermofisher.com/us/en/home/life-science/protein-biology/protein-biology-learning-center/protein-biology-resource-library/pierce-protein-methods/chemistry-crosslinking.html, 16 pages (accessed on Nov. 20, 2019) (Year: 2019).*

Nieberler et al., Cancer 9:1-33 (2017) (Year: 2017).*

"PDMS: The Favorite Material of Microfluidics (For Now)," MicroFluidic Future, available online at https://www.microfluidicfuture.com/blog/pdms-the-favorite-material-of-microfluidics-for-now, 6 pages (2011) (Year: 2011).*

Ali et al., BioRes Open Access 2:241-249 (2013) (Year: 2013).*

McGinnity, D. F. et al. (2004) "Evaluation of Fresh and Cryopreserved Hepatocytes as in Vitro Drug Metabolism Tools for the Prediction of Metabolic Clearance," *Drug Metabolism and Disposition* 32(11), 1247.

Schön, M. R. et al. (2001) "Liver Transplantation After Organ Preservation With Normothermic Extracorporeal Perfusion," *Annals of Surgery* 233(1), 114-123.

PCT International Search Report of International Application No. PCT/US2017/041762 dated Sep. 29, 2017.

Great Britain Office Action for the Great Britain Patent Application No. GB 1711206.1 dated Apr. 25, 2018.

Gaudet, C. et al. (2003) "Influence of Type I Collagen Surface Density on Fibroblast Spreading, Motility, and Contractility," *Biophysical Journal* 85(5), 3329-3335.

Sung, M. H. et al. (2006) "Hydrophilic Surface Modification of PDMS Using Atmospheric RF Plasma," *Journal of Physics: Conference Series* 34(1), 656.

Trappmann, B. et al. (2012) "Extracellular-matrix tethering regulates stem-cell fate," *Nature Materials* 11, 642.

Zamir, E. et al. (2001) "Molecular complexity and dynamics of cell-matrix adhesions," *Journal of Cell Science* 114(20), 3583.

Li, B. et al. (2006) "RGD peptide-conjugated poly(dimethylsiloxane) promotes adhesion, proliferation, and collagen secretion of human fibroblasts," *Journal of Biomedical Materials Research Part A* 79A(A), 989-998.

Zhang, L. et al. (2011) "Construction and application of a functional microfluidic cell chip," *Journal of Third Military Medical University* 55(24), 2575-2578.

Singapore Written Opinion for the Singapore Patent Application No. 11201901000X dated Jan. 11, 2022.

* cited by examiner

SULFO-SANPAH
SULFOSUCCINIMIDYL 8-[4'-AZIDO-2'-NITROPHENYLAMINOHEXANOATE
MW 492.40
SPACER ARM 18.2Å

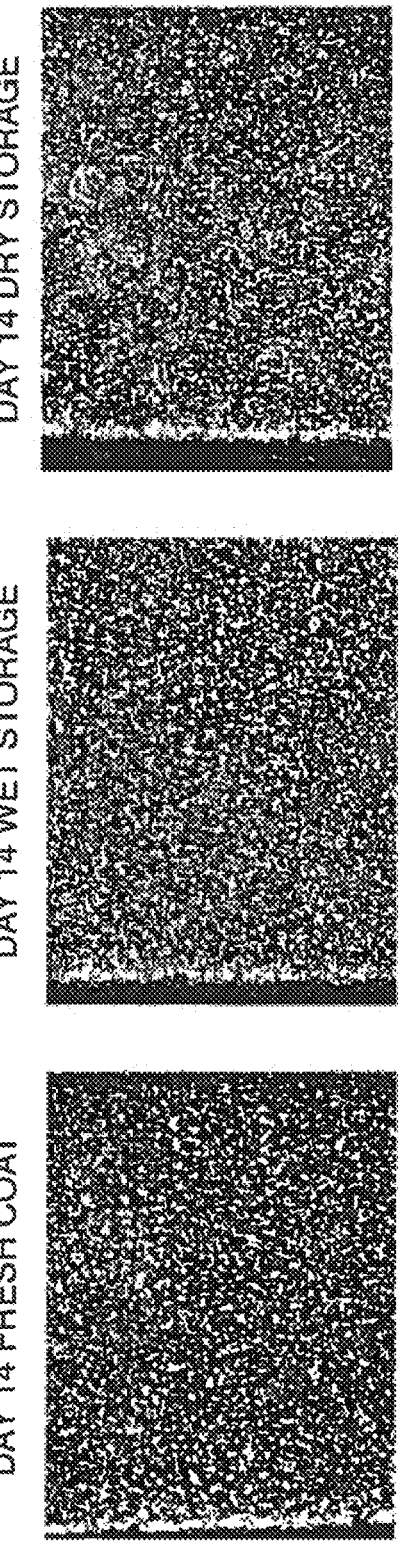

COMPOSITIONS AND METHODS OF CELL ATTACHMENT

FIELD OF THE INVENTION

The present invention contemplates compositions, devices and methods of improving adhesion, attachment, and/or differentiation of cells in a microfluidic device or chip. In one embodiment, ECM protein(s) is covalently coupled to the surface of a microchannel of a microfluidic device. The microfluidic devices can be either stored, or immediately used for culture and/or support of living cells such as mammalian cells, and/or for simulating a function of a tissue, e.g., a liver tissue, muscle tissue, etc. Extended adhesion and viability with sustained function over time is observed.

BACKGROUND

Cell adhesion is a central mechanism that ensures the structural integrity of tissue and is often a requirement for its biological function. The most prominent cell-matrix adhesion structures are so-called focal contacts. Focal contacts consist of large patches of transmembrane adhesion receptors from the integrin-family. These integrin patches in the cell membrane can reach lateral sizes of several micrometers. On the extracellular side, integrin binds to ligands such as the ECM proteins collagen, fibronectin and vitronectin. On the intracellular side, the receptors are linked to the actin cytoskeleton via a cytoplasmic plaque composed of many different proteins, including talin, vinculin, paxillin, and $\alpha$-actinin. See Zamir and Geiger, "Molecular complexity and dynamics of cell-matrix adhesions," *J. Cell Science* 114: 3583 (2001). This connection to the cytoskeleton, which is often organized in the form of stress fibers, allows transmitting forces between cells and the ECM through focal contacts. Adhesions between cells and the extracellular matrix (ECM) are known to modulate numerous cellular events.

Cell adhesion is also important in cell culture. Researchers have attempted to optimize the culture conditions of cells by extracellular matrix (ECM) coating of the culture dish, culture well, or culture channel. However, these ECMs are often applied generically with mixed results, depending on the cell type and culture conditions. What is needed is a more specific use of ECMs in the context of specific cell types and culture conditions.

SUMMARY OF THE INVENTION

The present invention contemplates compositions, devices and methods of improving adhesion, attachment, differentiation, longevity, quiescence, or biological function of cells in a microfluidic device or chip. In one embodiment, one or more proteins (e.g. ECM proteins) or peptides (e.g. RGD) are covalently coupled to the surface of a microfluidic device, whether within a microchannel or an open structure. The microfluidic devices can stored and used later, or they can be immediately used for culture and/or support of living cells such as mammalian cells, and/or for simulating a function of a tissue, e.g., a liver tissue, muscle tissue, etc., or simulating a function of an organ, e.g., a Liver-Chip, a Lung-Chip, etc. Extended adhesion and viability with sustained function over time is observed. In one embodiment, the microchannel comprises a surface comprising a silicone polymer. In one embodiment, the silicone polymer is polydimethylsiloxane or "PDMS." In one embodiment, the ECM protein is covalently coupled to a PDMS surface using a crosslinker, such as the heterobifunctional linker N-sulphosuccinimidyl-6-(4'-azido-2'-nitrophenylamino) hexanoate (Sulfo-SANPAH). In one embodiment, the living cells are exposed to fluid flow, the fluid flow providing shear stress.

In one embodiment, the present invention contemplates a method of culturing cells, comprising: a) providing a microfluidic device comprising a microchannel comprising a surface, said microchannel in fluidic communication with a fluid source comprising fluid; b) covalently attaching one or more proteins or peptides to said microchannel surface so as to create a treated surface; c) seeding viable cells on said treated surface so as to create attached cells; c) flowing fluid from said fluid source through said microchannel so as to create flowing conditions; and d) culturing said attached cells under said flow conditions such that said cells remain attached and viable (e.g. viable for at least 14 days). It is not intended that the present invention be limited to any particular cell type; a variety of cell types are contemplates (including more than one cell type). In one embodiment, said cells are hepatocytes. It is not intended that the present invention be limited to any particular protein or peptide; a variety are contemplated, including mixtures. For example, in one embodiment, the covalently attached protein is collagen. In another embodiment, a mixture of proteins are covalently attached, e,g. a mixture of collagen type I, fibronectin and collagen type IV. In yet another embodiment, the RGD peptide is attached (or a peptide comprising the RGD motif is attached). In one embodiment, the microchannel further comprises a membrane. In one embodiment, the membrane comprises PDMS. In one embodiment, the membrane comprises a crosslinker (e.g. covalently bound to the membrane). In one embodiment, the crosslinker is a bifunctional crosslinker. In one embodiment, the crosslinker is Sulfo-SANPAH (which is light activated with UV irradiation). In one embodiment, an extracellular matrix protein (e.g. laminin) is attached to the crosslinker (e.g. covalently bound) so as to provide an ECM-coated membrane. In one embodiment, the irradiated membrane is washed before the ECM attachment step. In one embodiment, the viable cells are further seeded onto the ECM-coated membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cells. In one embodiment, the skeletal muscle cells are human.

In one embodiment, the microchannel further comprises a micropatterned membrane. In one embodiment, the micropatterned membrane comprises PDMS. In one embodiment, a bifunctional crosslinker is attached to the micropatterned membrane. In one embodiment, the micropatterned membrane is in the flow channel of a microfluidic device. In one embodiment, the micropattern is parallel to the fluid flow. In one embodiment, the micropattern is perpendicular to the fluid flow. In one embodiment, an extracellular matrix protein (e.g. laminin) is attached to the crosslinker (e.g. covalently bound) so as to provide an ECM-coated micropatterned membrane. In one embodiment, the viable cells are further seeded onto the ECM-coated micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human ("hSKMCs"). In one embodiment, the skeletal muscle cells elongate in the grooves of the micropatterned membrane.

In one embodiment, the crosslinker is only attached to a portion of the membrane or the micropatterned membrane. In one embodiment, the portion where the crosslinker is not attached is covered with a mask (e.g. the crosslinker is light activated and the mask blocks the light) and the portion where the crosslinker is attached is unmasked. The mask may be adhesive material (e.g. tape) or non-adhesive material (e.g. metal or metal foil such as aluminum foil). In one embodiment, an extracellular matrix protein (e.g. laminin) is attached to the crosslinker (e.g. covalently bound) in the unmasked portion so as to provide an ECM-coated membrane or micropatterned membrane. In one embodiment, the viable cells are further seeded onto the ECM-coated portion of the membrane or micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human.

It is not intended that the present invention be limited to the method by which micropatterns are introduced into the membrane. In one embodiment, the micropatterns are introduced into the membrane through the use of an existing micropatterned silicon wafer mold; PDMS material can be spin coated on the mold and cured (the membrane is thereafter removed from the mold and used to assemble a microfluidic device or chip). In one embodiment, the micropattern is embossed using an existing micropatterned silicon wafer using both heat and pressure.

The present invention contemplates that in certain embodiments, the surface can be treated prior to step b). A variety of surface treatments (e.g. chemical vapor deposition, plasma oxidation, Corona, RF plasma, etc.) are possible. For example, in one embodiment, the present invention contemplates wherein said microchannel surface is PDMS and wherein said PDMS is plasma treated prior to step b).

It is not intended that the present invention be limited by the manner in which the proteins or peptides are covalently attached. In one embodiment, a crosslinker is used. In another embodiment, a bifunctional crosslinker is used. In a preferred embodiment, the protein or peptide is covalently attached to said microchannel surface using N-sulphosuccinimidyl-6-(4'-azido-2'-nitrophenylamino) hexanoate.

The present invention contemplates that the cells will be remain viable and can be tested to confirm this. However, it is not intended that the present invention be limited to a particular viability test. In one embodiment, the method further comprises e) assessing viability by measuring the level of activity of one or more cellular enzymes. A variety of enzymes can be used for this purpose, including but not limited to, a CYP enzyme, a transaminase and the like. In another embodiment, the present invention contemplates that the method further comprises e) assessing viability by measuring the level of expression of one or more cellular proteins.

In yet another embodiment, the present invention contemplates a method of culturing specific cells, comprising: a) providing a microfluidic device comprising a microchannel comprising a surface, said microchannel in fluidic communication with a fluid source comprising fluid; b) covalently attaching one or more proteins or peptides to said microchannel surface so as to create a treated surface; c) seeding viable hepatocytes on said treated surface so as to create attached cells; c) flowing fluid from said fluid source through said microchannel so as to create flowing conditions; and d) culturing said attached cells under said flow conditions such that said cells remain attached and viable (e.g. viable for at least 14 days). It is not intended that the present invention be limited by the nature or species of hepatocytes. In one embodiment, said hepatocytes are dog hepatocytes. It is not intended that the present invention be limited to any particular protein or peptide; a variety are contemplated, including mixtures. For example, in one embodiment, the covalently attached protein is collagen. In another embodiment, a mixture of proteins are covalently attached, e,g. a mixture of collagen type I, fibronectin and collagen type IV. In yet another embodiment, the RGD peptide is attached (or a peptide comprising the RGD motif is attached). In one embodiment, the microchannel further comprises a membrane. In one embodiment, the membrane comprises PDMS. In one embodiment, the membrane comprises a crosslinker (e.g. covalently bound to the membrane). In one embodiment, the crosslinker is a bifunctional crosslinker. In one embodiment, the crosslinker is Sulfo-SANPAH (which is light activated with UV irradiation). In one embodiment, an extracellular matrix protein (e.g. laminin) is attached to the crosslinker (e.g. covalently bound) so as to provide an ECM-coated membrane. In one embodiment, the irradiated membrane is washed before the ECM attachment step. In one embodiment, the viable cells are further seeded onto the ECM-coated membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human.

In one embodiment, the microchannel further comprises a micropatterned membrane. In one embodiment, the micropatterned membrane comprises PDMS. In one embodiment, a bifunctional crosslinker is attached to the micropatterned membrane. In one embodiment, the micropatterned membrane is in the flow channel of a microfluidic device. In one embodiment, the micropattern is parallel to the fluid flow. In one embodiment, the micropattern is perpendicular to the fluid flow. In one embodiment, an extracellular matrix protein (e.g. laminin) is attached to the crosslinker (e.g. covalently bound) so as to provide an ECM-coated micropatterned membrane. In one embodiment, the viable cells are further seeded onto the ECM-coated micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human. In one embodiment, the skeletal muscle cells elongate in the grooves of the micropatterned membrane.

In one embodiment, the crosslinker is only attached to a portion of the membrane or the micropatterned membrane. In one embodiment, the portion where the crosslinker is not attached is covered with a mask (e.g. the crosslinker is light activated and the mask blocks the light) and the portion where the crosslinker is attached is unmasked. The mask may be adhesive material or non-adhesive material (e.g. metal or metal foil such as aluminum foil). In one embodiment, an extracellular matrix protein (e.g. laminin) is attached to the crosslinker (e.g. covalently bound) in the unmasked portion so as to provide an ECM-coated membrane or micropatterned membrane. In one embodiment, the viable cells are further seeded onto the ECM-coated portion of the membrane or micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human.

It is not intended that the present invention be limited to the method by which micropatterns are introduced into the membrane. In one embodiment, the micropatterns are introduced into the membrane through the use of an existing micropatterned silicon wafer mold; PDMS material can be spin coated on the mold and cured (the membrane is thereafter removed from the mold and used to assemble a microfluidic device or chip). In one embodiment, the micropattern is embossed using an existing micropatterned silicon wafer using both heat and pressure.

It is not intended that the present invention be limited by the manner in which the proteins or peptides are covalently attached. In one embodiment, a crosslinker is used. In another embodiment, a bifunctional crosslinker is used. In a preferred embodiment, the protein or peptide is covalently attached to said microchannel surface using N-sulphosuccinimidyl-6-(4'-azido-2'-nitrophenylamino) hexanoate.

The present invention contemplates that the cells will be remain viable and can be tested to confirm this. However, it is not intended that the present invention be limited to a particular viability test. In one embodiment, the method further comprises e) assessing viability by measuring the level of activity of one or more cellular enzymes. A variety of enzymes can be used for this purpose, including but not limited to, a CYP enzyme, a transaminase and the like. In another embodiment, the present invention contemplates that the method further comprises e) assessing viability by measuring the level of expression of one or more cellular proteins.

The present invention contemplates that in certain embodiments, the surface can be treated prior to step b). A variety of surface treatments (e.g. chemical vapor deposition, plasma oxidation, Corona, RF plasma, etc.) are possible. For example, in one embodiment, the present invention contemplates wherein said microchannel surface is PDMS and wherein said PDMS is plasma treated prior to step b).

As noted above, cells need not be immediately cultured in the device, i.e. the device can be stored with the covalently attached protein(s). In one embodiment, the present invention contemplates a method of treating a microfluidic device, comprising: a) providing a microfluidic device comprising a microchannel comprising a surface, said microchannel in fluidic communication with a fluid source comprising fluid; b) covalently attaching one or more proteins or peptides to said microchannel surface so as to create a treated surface; and c) storing said microfluidic device. It is not intended that the present invention be limited to the precise storage conditions. However, the storing is typically done at a controlled temperature below room temperature, e.g. between 2 and 10° C., in a refrigerator or other cooling device. It is not intended that the present invention be limited to dry or wet storage. In one embodiment, said one or more covalently attached proteins is collagen I and it is stored wet or dry (more preferred). In one embodiment, said one or more covalently attached proteins is laminin and it is stored wet (preferred) or dry. Laminin and/or Matrigel are contemplated for a variety of chips, including Intestine-on-Chip, Blood Brain Barrier (BBB)-on-Chip, and NeuroMuscular Junction (NMJ)-on-Chip. In one embodiment, the microchannel further comprises a membrane. In one embodiment, the membrane comprises PDMS. In one embodiment, the membrane comprises a crosslinker (e.g. covalently bound to the membrane). In one embodiment, the crosslinker is a bifunctional crosslinker. In one embodiment, the crosslinker is Sulfo-SANPAH (which is light activated with UV irradiation). In one embodiment, an extracellular matrix protein (e.g. laminin) is attached to the crosslinker (e.g. covalently bound) so as to provide an ECM-coated membrane. In one embodiment, the irradiated membrane is washed before the ECM attachment step. In one embodiment, the viable cells are further seeded onto the ECM-coated membrane. In one embodiment, the viable cells are neurons. In one embodiment, the viable cells are motor neurons. In one embodiment, the viable cells are hepatocyte. In one embodiment, the viable cells are skeletal muscle cell. In one embodiment, the skeletal muscle cells are human.

In one embodiment, the microchannel further comprises a micropatterned membrane. In one embodiment, the micropatterned membrane comprises PDMS. In one embodiment, a bifunctional crosslinker is attached to the micropatterned membrane. In one embodiment, the micropatterned membrane is in the flow channel of a microfluidic device. In one embodiment, the micropattern is parallel to the fluid flow. In one embodiment, the micropattern is perpendicular to the fluid flow. In one embodiment, an extracellular matrix protein (e.g. laminin) is attached to the crosslinker (e.g. covalently bound) so as to provide an ECM-coated micropatterned membrane. In one embodiment, the viable cells are further seeded onto the ECM-coated micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human. In one embodiment, the skeletal muscle cells elongate in the grooves of the micropatterned membrane.

In one embodiment, the crosslinker is only attached to a portion of the membrane or the micropatterned membrane. In one embodiment, the portion where the crosslinker is not attached is covered with a mask (e.g. the crosslinker is light activated and the mask blocks the light) and the portion where the crosslinker is attached is unmasked. The mask may be adhesive material or non-adhesive material (e.g. metal or metal foil such as aluminum foil). In one embodiment, an extracellular matrix protein (e.g. laminin) is attached to the crosslinker (e.g. covalently bound) in the unmasked portion so as to provide an ECM-coated membrane or micropatterned membrane. In one embodiment, the viable cells are further seeded onto the ECM-coated portion of the membrane or micropatterned membrane. In one embodiment, the viable cells are neurons. In one embodiment, the viable cells are motor neurons. In one embodiment, the viable cells are hepatocyte. In one embodiment, the viable cells are muscle cells. In one embodiment, the viable cells are skeletal muscle cell. In one embodiment, the skeletal muscle cells are human.

It is not intended that the present invention be limited to the method by which micropatterns are introduced into the membrane. In one embodiment, the micropatterns are introduced into the membrane through the use of an existing micropatterned silicon wafer mold; PDMS material can be spin coated on the mold and cured (the membrane is thereafter removed from the mold and used to assemble a microfluidic device or chip). In one embodiment, the micropattern is embossed using an existing micropatterned silicon wafer using both heat and pressure.

The storage may be for a time period of 1, 2, 3, 4, 5, 6, 7, 8, 9, 10, 11, 12, 13, 14 or more days—and even may be done for 3, 4 or 5 weeks. After storage, it is contemplated that cells will be added. For example, in one embodiment, the present invention contemplates that the method further comprises: d) seeding viable cells on said treated surface so as to create attached cells; e) flowing fluid from said fluid source through said microchannel so as to create flowing conditions; and f) culturing said attached cells under said flow conditions such that said cells remain attached and viable (e.g. viable for at least 14 days).

Again, any type of cell (or combination of cells) can be seeded. Cells may be of any cell type from a multicellular structure, including nematodes, amoebas, up to mammals such as humans. The cell types seeded on the device may simply depend on the type of organ (lung, liver, intestine, brain, kidney etc.) or organ function one wishes to mimic, and the tissues that comprise those organs. One can also co-culture various stem cells, such as bone marrow cells, induced adult stem cells, embryonal stem cells or stem cells isolated from adult tissues. In one embodiment said cells are hepatocytes. In one embodiment, said cells are Human Umbilical Vein Endothelial Cells (HUVECs). In one embodiment, said cells are intestinal cells. In one embodiment, said cells are from patients with a disease, i.e. diseased cells. In one embodiment, said cells are from healthy controls.

The present invention contemplates that in certain embodiments, the surface can be treated prior to step b). A variety of surface treatments (e.g. chemical vapor deposition, plasma oxidation, Corona, RF plasma, etc.) are possible. For example, in one embodiment, the present invention contemplates wherein said microchannel surface is PDMS and wherein said PDMS is plasma treated prior to step b).

A noted above, the cells may be tested for viability. On the other hand, the cells may be put to other tests, such as tests directed at basic biological science, life science research, drug discovery and development, drug safety testing, chemical and biological assays, as well as tissue and organ engineering. In an embodiment, the organ mimic device can be used as microvascular network structures for basic research in cardiovascular, cancer, and organ-specific disease biology. Furthermore, one or more embodiments of the device find application in organ assist devices for liver, kidney, lung, intestine, bone marrow, and other organs and tissues, as well as in organ replacement structures.

It is not intended that the devices be limited in their use. In one embodiment, there are used for: the identification of markers of disease; assessing efficacy of anti-cancer therapeutics; testing gene therapy vectors; drug development; screening; studies of cells, especially stem cells and bone marrow cells; studies on biotransformation, absorption, clearance, metabolism, and activation of xenobiotics; studies on bioavailability and transport of chemical or biological agents across epithelial or endothelial layers; studies on transport of biological or chemical agents across the blood-brain barrier, studies on transport of biological or chemical agents across the intestinal epithelial barrier, studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical or biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; studies on gene transcription in response to chemical or biological agents; studies on protein expression in response to chemical or biological agents; studies on changes in metabolism in response to chemical or biological agents. The organ mimic device can also be used to screen on the cells, for an effect of the cells on the materials (for example, in a manner equivalent to tissue metabolism of a drug).

In one embodiment, the present invention contemplates a method of culturing cells, comprising: a) providing a microfluidic device comprising a microchannel comprising a surface, said microchannel in fluidic communication with a fluid source comprising fluid; b) covalently attaching a bifunctional crosslinker to said surface to create attached crosslinker, c) covalently attaching one or more proteins or peptides to said attached crosslinker as to create a treated surface; d) seeding viable cells on said treated surface so as to create attached cells; e) flowing fluid from said fluid source through said microchannel so as to create flowing conditions; and f) culturing said attached cells under said flow conditions such that said cells remain attached and viable for at least 7 days. In one embodiment, said surface is a membrane and said membrane is micropatterned. In one embodiment, said cells are muscle cells that align with said micropattern (of the micropatterned membrane). In one embodiment, said crosslinker is activated with UV light in the presence of a mask (so that light is blocked from contacting a portion of said surface).

In one embodiment, the present invention contemplates a method of culturing cells, comprising: a) providing a microfluidic device comprising a surface; b) covalently attaching one or more proteins or peptides to said surface using a crosslinker so as to create a treated surface; c) seeding viable cells on said treated surface so as to create attached cells; and d) culturing said attached cells such that said cells remain attached and viable for at least 7 days. In one embodiment, the microfluidic device further comprises a microchannel, said surface disposed within said microchannel, and wherein said microchannel is in fluidic communication with a fluidic source comprising fluid, the method further comprising the step of flowing fluid from said fluid source through said microchannel so as to create flow conditions, and wherein said culturing in d) further comprises culturing said attached cells under said flow conditions. In one embodiment, the attached cells further remain viable for at least 14 days. In one embodiment, the attached cells further remain functional for at least 7 days. In one embodiment, the attached cells further remain functional for at least 14 days. In one embodiment, the crosslinker comprises at least one light-reactive portion and at least one chemically reactive portion. In one embodiment, the crosslinker further comprises at least one spacer portion. In one embodiment, the at least one light-reactive portion is selected from the group consisting of a nitrophenyl, a diazirine and an azide. In one embodiment, the at least one chemically reactive portion is selected from the group consisting of an NHS-ester, a sulfo-NHS-ester, isocyanate, isothiocyanate, imidoester, maleimide, pyridyldithiol, and hydrazide. In one embodiment, the crosslinker is selected from the group consisting of sulfo-SANPA, SANPAH, SDA, sulfo-SDA, LC-SDA, sulfo-LC-SDA, ANB-NOS, SDAD, and sulfo-SDAD. In one embodiment, the surface comprises PDMS. In one embodiment, the surface is plasma treated prior to step b). In one embodiment, the cells are hepatocytes. In one embodiment, the method further comprises step e) assessing viability by measuring the level of activity of one or more cellular enzymes. In one embodiment, the cellular enzyme is a CYP enzyme. In one embodiment, the cellular enzyme is a transaminase. In one embodiment, the method further comprises step e) assessing viability by measuring the level of expression of one or more cellular proteins. In one embodiment, the one or more proteins comprises collagen. In one embodiment, the one or more proteins comprises a mixture of collagen type I, fibronectin and collagen type IV. In one embodiment, the one or more peptides comprises RGD or a peptide comprising the RGD motif. In one embodiment, wherein RGD is covalently attached to said surface using N-sulphosuccinimidyl-6-(4'-azido-2'-nitrophenylamino) hexanoate. In one embodiment, the covalently attaching one or more proteins or peptides in step b) further comprises: i) introducing said crosslinker or a solution containing said crosslinker to contact said surface and permitting said crosslinker or said solution containing said crosslinker to react with said surface; and ii) introducing at least one protein or peptide, or a solution containing at least one protein or peptide to contact said surface. In one embodiment, the covalently attaching one or more proteins or peptides in b) further comprises exposing at least a portion of said surface to light. In one embodiment, the light comprises UV light. In one embodiment, the exposing comprises exposing a selected area or pattern for the covalent attachment of at least a portion of said one or more proteins or peptides. In one embodiment, the exposing comprises masking said light so as to select said selected area or pattern. In one embodiment, the exposing comprises projecting a light pattern so as to select said selected area or pattern. In one embodiment, the exposing comprises rastering light so as to select said selected area or pattern. In one embodiment, the selected area or pattern comprises a linear pattern. In one embodiment, the cells comprise muscle cells or muscle-like cells that align with respect to said selected area of pattern. In one embodiment, the covalently attaching one or more proteins or peptides in b) further comprises introducing said crosslinker to contact only one or more selected areas of said microfluidic device. In one embodiment, the microfluidic device further comprises a porous membrane. In one embodiment, the porous membrane comprises said surface.

In one embodiment, the present invention contemplates a method of treating a microfluidic device, comprising: a) providing a microfluidic device comprising a surface; b) covalently attaching one or more proteins or peptides to said surface using a crosslinker so as to create a treated surface; and c) storing said microfluidic device. In one embodiment, the microfluidic device comprises a microchannel, said surface disposed within said microchannel. In one embodiment, the storing in step c) comprises storing said surface dry. In one embodiment, the storing in step c) comprises storing said surface wet. In one embodiment, the crosslinker comprises at least one light-reactive portion, at least one chemically reactive portion. In one embodiment, the crosslinker further comprises at least one spacer portion. In one embodiment, the at least one light-reactive portion is selected from the group consisting of a nitrophenyl, a diazirine and an azides. In one embodiment, the at least one chemically reactive portion is selected from the group consisting of NHS-ester, sulfo-NHS-ester, isocyanate, isothiocyanate, imidoester, maleimide, pyridyldithiol, and hydrazide. In one embodiment, the crosslinker is selected from the list comprising: sulfo-SANPAH, SANPAH, SDA, sulfo-SDA, LC-SDA, sulfo-LC-SDA, ANB-NOS, SDAD, sulfo-SDAD. In one embodiment, the storing is done at a controlled temperature below room temperature. In one embodiment, the storing is done at between 2 and 10° C. In one embodiment, the one or more covalently attached proteins is collagen I. In one embodiment, the covalently attached collagen I is stored dry. In one embodiment, the one or more covalently attached proteins is laminin. In one embodiment, the covalently attached laminin is stored wet. In one embodiment, the method further comprises step d) seeding viable cells on said treated surface so as to create attached cells; and f) culturing said attached cells such that said cells remain attached and viable for at least 7 days. In one embodiment, the microfluidic device further comprises a microchannel, said surface disposed within said microchannel, and wherein said microchannel is in fluidic communication with a fluidic source comprising fluid, the method further comprising flowing fluid from said fluid source through said microchannel so as to create flow conditions, and wherein culturing in f) further comprises culturing said attached cells under said flow conditions. In one embodiment, the attached cells further remain viable for at least 14 days. In one embodiment, the attached cells further remain functional for at least 7 days. In one embodiment, the attached cells further remain functional for at least 14 days. In one embodiment, the attached cells are hepatocytes. In one embodiment, the surface comprises PDMS. In one embodiment, the surface is plasma treated prior to step b). In one embodiment, the covalently attaching one or more proteins or peptides in b) further comprises: i) introducing said crosslinker or a solution containing said crosslinker to contact said surface and permitting said crosslinker or said solution containing said crosslinker to react with said surface; and ii) introducing at least one protein or peptide, or a solution containing at least one protein or peptide to contact said surface. In one embodiment, the covalently attaching one or more proteins or peptides in b) further comprises exposing at least a portion of said surface to light. In one embodiment, the light comprises UV light. In one embodiment, the exposing comprises exposing a selected area or pattern for the covalent attachment of at least a portion of said one or more proteins or peptides. In one embodiment, the exposing comprises masking said light so as to select said selected area or pattern. In one embodiment, the exposing comprises projecting a light pattern so as to select said selected area or pattern. In one embodiment, the exposing comprises rastering light so as to select said selected area or pattern. In one embodiment, the selected area or pattern comprises a linear pattern. In one embodiment, the cells comprise muscle cells or muscle-like cells that align with respect to said selected area or pattern. In one embodiment, the covalently attaching one or more proteins or peptides in b) further comprises introducing said crosslinker to contact one or more selected areas of said microfluidic device. In one embodiment, the microfluidic device further comprises a porous membrane. In one embodiment, the membrane comprises said surface.

In one embodiment, a method of culturing cells, comprising: a) providing a microfluidic device comprising a microchannel comprising a surface, said microchannel in fluidic communication with a fluid source comprising fluid; b) covalently attaching a crosslinker to said surface to create attached crosslinker, c) covalently attaching one or more proteins or peptides to said attached crosslinker as to create a treated surface; d) seeding viable cells on said treated surface so as to create attached cells; e) flowing fluid from said fluid source through said microchannel so as to create flowing conditions; and f) culturing said attached cells under said flow conditions such that said cells remain attached and viable for at least 7 days. In one embodiment, the surface is a membrane and said membrane is micropatterned. In one embodiment, the cells are muscle cells that align with said micropattern. In one embodiment, the crosslinker is activated with UV light in the presence of a mask.

In one embodiment, the present invention contemplates a kit comprising: a) a microfluidic device comprising a surface; b) a crosslinker comprising at least one light-reactive portion, and at least one chemically reactive portion; c) at least one protein or peptide; and d) a set of instructions. In one embodiment, the kit further comprises cells.

In one embodiment, a method of culturing cells, comprising: a) providing a microfluidic device comprising a surface; b) covalently attaching one or more proteins or peptides to said surface at a selected area or pattern using a crosslinker so as to create a treated surface; c) seeding viable cells on said treated surface so as to create attached cells; and d) culturing said attached cells. In one embodiment, the microfluidic device comprises a microchannel, said surface disposed within said microchannel, and wherein said microchannel is in fluidic communication with a fluidic source comprising fluid, the method further comprising flowing fluid from said fluid source through said microchannel so as to create flow conditions, and wherein culturing in d) further comprises culturing said attached cells under said flow conditions. In one embodiment, the crosslinker comprises at least one light-reactive portion, at least one chemically reactive portion. In one embodiment, the crosslinker further comprises at least one spacer portion. In one embodiment, the at least one light-reactive portion is selected from the group consisting of a nitrophenyl, a diazirine and an azides. In one embodiment, the at least one chemically reactive portion is selected from the group consisting of NHS-ester, sulfo-NHS-ester, isocyanate, isothiocyanate, imidoester, maleimide, pyridyldithiol, and hydrazide. In one embodiment, the crosslinker is selected from the group consisting of sulfo-SANPAH, SANPAH, SDA, sulfo-SDA, LC-SDA, sulfo-LC-SDA, ANB-NOS, SDAD, and sulfo-SDAD. In one embodiment, the surface comprises PDMS. In one embodiment, the surface is plasma treated prior to step b). In one embodiment, the attached cells further remain viable for at least 7 days. In one embodiment, the attached cells further remain functional for at least 7 days. In one embodiment, the attached cells further remain functional for at least 14 days. In one embodiment, the method further comprises storing said microfluidic device before step c). In one embodiment, the covalently attaching one or more proteins or peptides in b) further comprises: i) introducing said crosslinker or a solution containing said crosslinker to contact said surface and permitting said crosslinker or said solution containing said crosslinker to react with said surface; and ii) introducing at least one protein or peptide, or a solution containing at least one protein or peptide to contact said surface. In one embodiment, the covalently attaching one or more proteins or peptides in b) further comprises exposing at least a portion of said surface to light. In one embodiment, the light comprises UV light. In one embodiment, the exposing comprises masking said light so as to select said selected area or pattern. In one embodiment, the exposing comprises projecting a light pattern so as to select said selected area or pattern. In one embodiment, the exposing comprises rastering light so as to select said selected area or pattern. In one embodiment, the selected area or pattern comprises a linear pattern. In one embodiment, the cells comprise muscle cells or muscle-like cells that align with respect to said selected area or pattern. In one embodiment, the microfluidic device further comprises a porous membrane. In one embodiment, the membrane comprises said surface.

In one embodiment, the present invention contemplates a microfluidic device for culturing cells, comprising a) a surface; b) one or more proteins or peptides attached to at least one portion of said surface by a crosslinker, said crosslinker comprising a light-reactive portion and a chemically reactive portion; wherein at least one chemical moiety of said light-reactive portion is covalently attached to said surface, and at least one chemical moiety of said chemically reactive portion is covalently attached to said one or more proteins or peptides. In one embodiment, the device further comprises a microchannel, said surface disposed within said microchannel, and wherein said microchannel is in fluidic communication with a fluidic source. In one embodiment, the at least one chemical moiety of said light-reactive portion is selected from the group consisting of a reacted nitrophenyl, a reacted diazirine and a reacted azide. In one embodiment, the at least one chemical moiety of said chemically reactive portion is selected from the group consisting of a reacted NHS-ester, a reacted sulfo-NHS-ester, a reacted isocyanate, a reacted isothiocyanate, a reacted imidoester, a reacted maleimide, a reacted pyridyldithiol, and reacted hydrazide. In one embodiment, the crosslinker is selected from the group consisting of sulfo-SANPAH, SANPAH, SDA, sulfo-SDA, LC-SDA, sulfo-LC-SDA, ANB-NOS, SDAD and sulfo-SDAD. In one embodiment, the surface comprises PDMS. In one embodiment, the at least one portion of said surface comprises a selected pattern. In one embodiment, the selected pattern comprises a linear pattern. In one embodiment, the device further comprises cells disposed in contact with said one or more proteins or peptides. In one embodiment, the cells comprise muscle cells or muscle-like cells that align with respect to said selected pattern. In one embodiment, the microfluidic device further comprises a porous membrane. In one embodiment, the membrane comprises said at least one portion of said surface.

Definitions

The term "channels" refer to pathways (whether straight, curved, single, multiple, in a network, etc.) through a medium (e.g., silicon, glass, polymer, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. It is not intended that the present invention be limited to only certain microchannel geometries. In one embodiment, a four-sided microchannel is contemplated. In another embodiment, the microchannel is circular (in the manner of a tube) with curved walls. In yet another embodiment, a combination of circular or straight walls is used.

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

The term "arginylglycylaspartic acid" or "RGD" refers to a tripeptide composed of L-arginine, glycine and L-aspartic acid. RGD and ROD-peptides (i.e. peptides that are more than 3 amino acids in length that contain the ROD motif), such as GRGDSP, are implicated in cellular attachment via integrins.

The term "microfluidic device" refers to a substrate comprising at least one channel that is configured to support fluid flow. Such a device may be constructed out of a variety of materials including, but not limited to, quartz, glass, plastic and/or PDMS or other polymer(s). For example, some microfluidic devices may comprise a microchip.

The term "seed" or "seeding" as used herein, refers to the attachment and growth of cells on a surface of a microfluidic device, for example, within a channel or on a membrane of the microfludic device.

The term "viable" as used herein, refers to any cell or group of cells that have demonstrated the capability of growing, dividing, developing and/or differentiating. Further, viability may be demonstrated by the identification of specific biomarkers known in the art for certain cell types and/or organs.

The term, "surface" as used herein refers to any substrate as well as solid substrates which may comprise an array, microarray or microdevice. In some cases, the substrate is solid and may comprise PDMS.

The term, "muscle" as used herein refers to any group of cells or tissue having contractile capability including, but not limited to, skeletal muscle, smooth muscle, cardiac muscle, myofibroblasts, pericytes, muscle cells and muscle-like cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7A-C are photographs showing examples of liver cells (hepatic cells) on ECM coated chips under various conditions. Chips were coated with collagen I and fibronectin and stored either dry or wet for one week. Cells were then added to the chips and cultured for 14 days. As a control, a chip was coated fresh (no storage) and cultured with cells for 14 days. No differences in cell attachment were observed in Liver sinusoidal endothelial cells (LSECs) or Hepatic cells (Hep). No differences in morphology were observed (LSEC and Hep). FIG. 7A is the control (fresh ECM coat) after 14 days of cell culture. FIG. 7B shows the results after 1 week wet storage and cell culture for 14 days. FIG. 7C shows the results after 1 week dry storage and cell culture for 14 days.

FIG. 10A-C images were taken at the point of the chip where the two channels join, the wall of the channel is the dark separator in the images. This is a top-down view. The gut function is assessed via barrier function (pApp, the system's permeability coefficient) and response to stimulation (using an inflammatory stimulus).

FIG. 11A shows wet storage of 3 weeks.

FIG. 13A: 10 µg/ml Laminin treated channels.

FIG. 13B: 50 µg/ml Laminin treated channels.

FIG. 13C: 100 µg/ml Laminin treated channels.

FIG. 14A: Motor neurons cultured in channels treated with 50 µg/ml Laminin.

FIG. 15A: Micropatterning perpendicular to channel fluid flow.

FIG. 16A: Phase contrast photomicrograph of skeletal muscle cell alignment along a micropatterned PDMS membrane.

FIG. 16B: Photomicrograph (10×) of hSKMC myotube nuclei development on Day 3 of culture on a micropatterned PDMS membrane.

FIG. 16C: Photomicrograph (10×) of hSKMC myotube nuclei development on Day 1 of culture on a micropatterned PDMS membrane.

FIG. 16D: Photomicrograph (20×) of hSKMC myotube nuclei development on Day 11 of culture on a micropatterned PDMS membrane.

FIG. 17A: Photomicrograph (10×) of actin development on a non-micropatterned PDMS membrane on culture Day 7.

FIG. 17B: Photomicrograph (20×) of actin development on a non-micropatterned PDMS membrane on culture Day 7.

FIG. 17C: Photomicrograph (10×) of actin development on a micropatterned PDMS membrane on culture Day 7.

FIG. 17D: Photomicrograph (20×) of actin development on a micropatterned PDMS membrane on culture Day 7.

FIG. 20A: An embossed PDMS membrane before cell attachment.

FIG. 20B: An embossed PDMS membrane subsequent to one day of cell attachment and culture.

FIG. 20C: An embossed PDMS membrane subsequent to six days of cell attachment and culture.

DETAILED DESCRIPTION OF THE INVENTION

Figure 1:
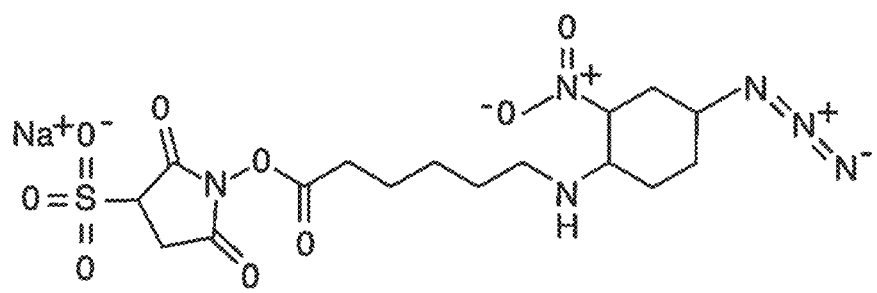
FIG. 1 shows the chemical structure of the commercially available heterobifunctional linker N-sulphosuccinimidyl-6-(4'-azido-2'-nitrophenylamino) hexanoate (Sulfo-SANPAH).
Figure 2:
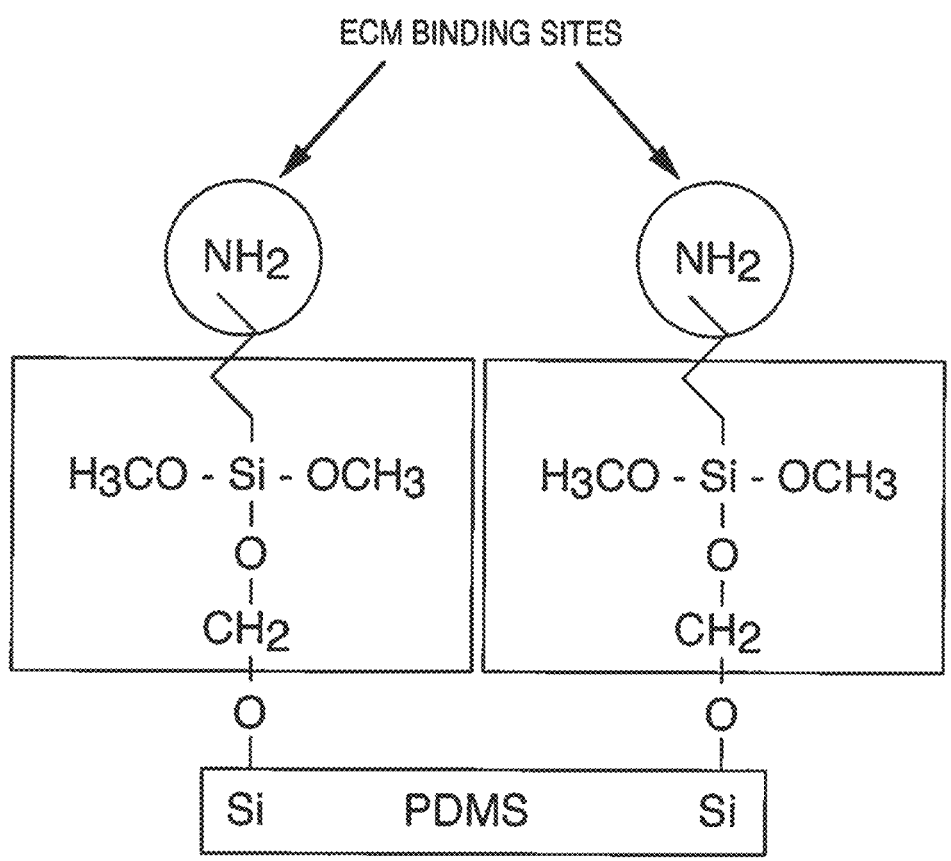
FIG. 2 shows the chemical surface modification to bind EMC protein to native PDMS via linker molecule.

Silicone elastomers, such as PDMS, are used in microfluidics. However, silicone polymers are hydrophobic and do not promote cell adhesion. Surface treatments (e.g. chemical vapor deposition, plasma oxidation, Corona, RF plasma, etc.) have been used to make such polymers more useful. See e.g. Hong et al., "Hydrophilic Surface Modification of PDMS Using Atmospheric RF Plasma," *Journal of Physics: Conference Series* 34 (2006) 656-661 (Institute of Physics Publishing). A microfluidic device (or portion thereof) made of a naturally hydrophobic material becomes hydrophilic upon such surface treatment. Nonetheless, cell attachment remains a problem, both in the short term and the long term. That is to say, some cells do not adhere well to surface treated PDMS at the outset; they exhibit low seeding levels. In the long term, cells (and even monolayers) can detach from the surface treated PDMS.

The present invention contemplates compositions, devices and methods of improving adhesion, attachment, and/or differentiation of cells in a microfluidic device or chip, and in particular, cells on a PDMS surface. In one embodiment, one or more proteins (e.g. ECM proteins) or peptides (e.g. RGD) are covalently coupled to the surface of a microchannel of a microfluidic device. The microfluidic devices can be stored and later used, or they can be immediately used for culture and/or support of living cells such as mammalian cells, and/or for simulating a function of a tissue, e.g., a liver tissue, muscle tissue, etc. Even under flow conditions, extended adhesion and viability with sustained function over time is observed.

The present invention contemplates microfluidic devices (or "chips") containing living cells recreate the physiological tissue-tissue interfaces and permit fluid flow. See U.S. Pat. No. 8,647,861, hereby incorporated by reference. Such devices subject the cells to shear stress. In contrast to static 2D culture, microchannels allow the perfusion of cell culture medium throughout the cell culture during in vitro studies and as such offer a more in vivo-like physical environment. In simple terms, an inlet port allows injection of fluids such as cell culture medium (and the like) into a microfluidic channel or chamber (with or without cells). In one embodiment, the present invention contemplates introduction of fluid into a cell-laden microfluidic channel or chamber. In a preferred embodiment, the cells are attached to one or more ECM proteins (e.g. laminin), which are in turn covalently attached to the microchannel surface. An outlet port then permits the exit of remaining fluid as well as harmful metabolic by-products.

The surface over which the fluid flows and to which the cells are attached (using the methods described herein) can be a surface of any material that is compatible to the fluid sample and cells. Exemplary materials for the fluid-contact surface can comprise glass, synthetic polymers (e.g., PDMS, polysulfonate, and polycarbonate), hydrogels, and a combination thereof.

One portion of a microchannel can be a membrane. For example, the floor of a microchannel can comprise a membrane, including a porous membrane. The microchannel (or portion thereof) or membrane can be coated with substances such as various cell adhesion promoting substances or ECM proteins, such as fibronectin, laminin or various collagen types or combinations thereof. For example, endothelial cells can attach to a collagen coated microchannel. While non-covalent coating can be used, it is preferred that such proteins and peptides be covalently attached, e.g. by use of a crosslinker or other chemistry.

It is not intended that the present invention be limited to the method by which one or more ECM proteins are covalently attached to the microchannel surface. In one embodiment, bifunctional crosslinkers are used. A variety of such crosslinkers are available commercially, including (but not limited to) the following compounds:

ANB-NOS (N-5-azido-2-nitrobenzoyloxysuccinimide) having the formula of:

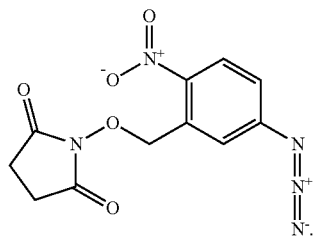

(I)

Sulfo-SAND (sulfosuccinimidyl 2-[m-azido-o-nitrobenzamido]ethyl-1,3'-dithiopropionate) having the formula of:

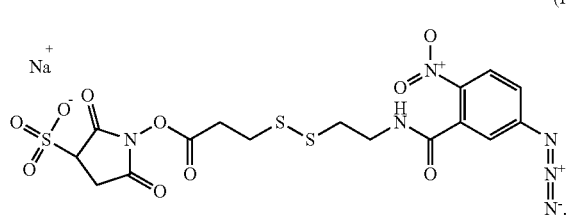

(II)

SANPAH (N-succinimidyl-6-[4'-azido-2'-nitrophenylamino]hexanoate) having the formula of:

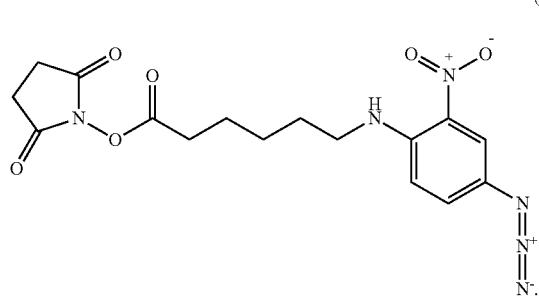

(III)

Sulfo-SANPAH (sulfosuccinimidyl-6-[4'-azido-2'-nitrophenylamino]hexanoate) having the formula of:

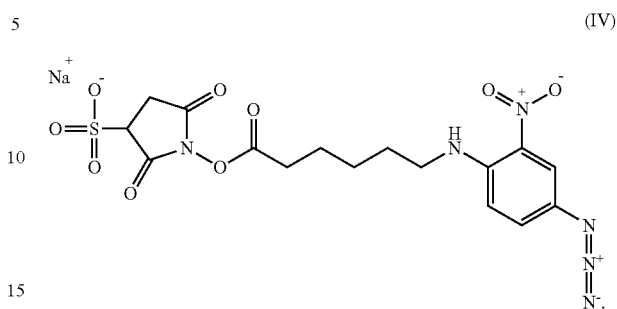

(IV)

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—NH$_2$) in pH 7-9 buffers to form stable amide bonds. The reaction results in the release of N-hydroxysuccinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

Figures 13A, 13B, 13C:
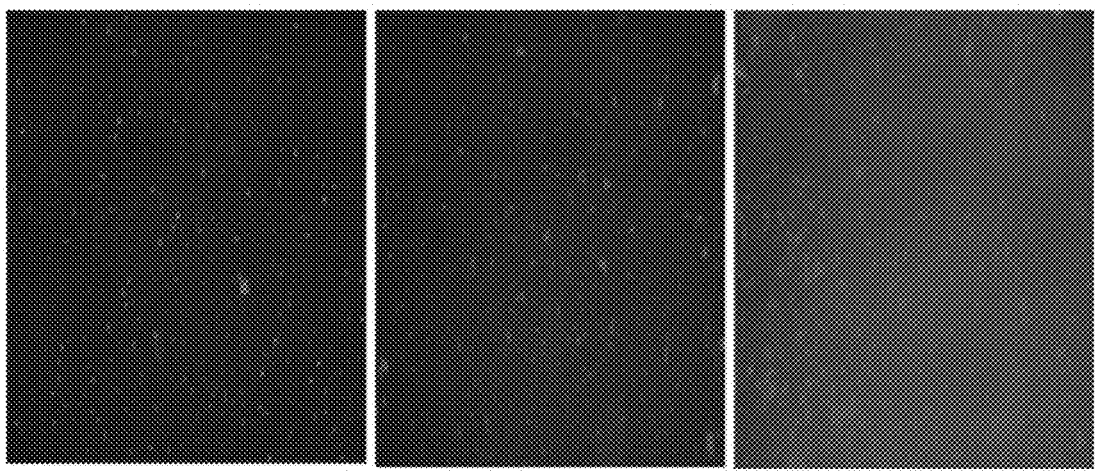
FIG. 13A-C presents exemplary data showing a concentration dependent effect of laminin binding subsequent to 500 µg/ml Sulfo-SANPAH (IV) treated channels.
Figure 14A:
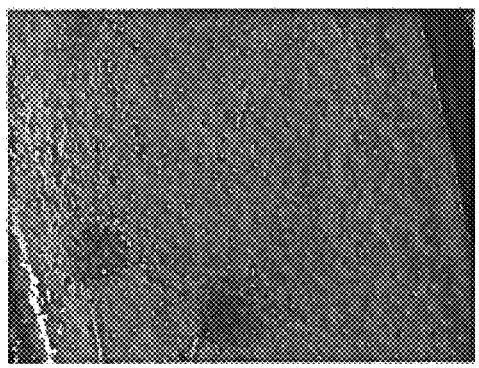
FIGS. 14A&B presents exemplary data showing a concentration dependent effect of laminin on the development and differentiation of motor neuron cells cultured on chips.
Figure 14B:
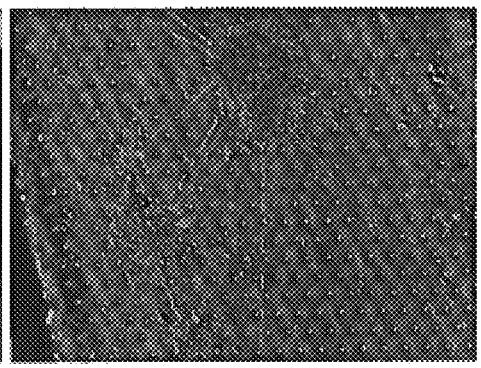
FIG. 14B: Motor neurons cultured in channels treated with 100 µg/ml Laminin.

The present invention is not to be limited to any particular crosslinker. In one embodiment, the crosslinkers of the current invention comprise three parts: a light-reactive portion, a linker, and a modifier-reactive portion. In one embodiment, the bifunctional crosslinkers are represented by the formula A-B-C, wherein A represents light-reactive portion, B represents a linker, and C represents modifier-reactive portion. The present invention is not to be limited to linear crosslinkers. In one embodiment, B can also be branched it multivalent. i.e. it can link one A to two Cs, 3As to 4Cs, etc, see FIG. 13. As a non-limiting example, sulfo-SANPAH uses a nitrophenyl azide group as the light-reactive portion, aminohexanoate as the linker, and sulfo-NHS ester as the modifier-reactive portion (in this case reacting with an amine group on the modifier), see FIGS. 14A&B. In one embodiment, light reactive portions may be selected from the group consisting of nitrophenyl, diazirine, and azides. The present invention is not to be limited to any particular linker. In one embodiment, the linker (B) are connected to light-reactive portion (A) through an amine bond and modifier-reactive portion (C) through an ester bond. In one embodiment, the linkers may be selected from the group consisting of polyethyleneglycols, alkanes, and olefins. In one embodiment, the modifier-reactive chemistry portion may be selected from the group consisting of NHS-ester (amine reactive), Sulfo-NHS-ester (amine reactive), Isocyanate (amine reactive), Isothiocyanate (amine reactive), Imidoester (amine reactive), Maleimide (sulfhydryl reactive), Pyridyldithiol (sulfhydryl reactive), and Hydrazide (aldehyde and ketone reactive). Specific examples of commercially available crosslinkers that fit this description include ANB-NOS, SDA, sulfo-SDA, LC-SDA, sulfo-LC- SDA, SDAD, sulfo-SDAD, and more (see Table 1). ANB-NOS is a short-arm (7.7 angstrom) crosslinker that contains an amine-reactive N-hydroxysuccinimide (NHS) ester and a photoactivatable nitrophenyl azide, also called N-5-azido-2-nitrobenzoyloxysuccinimide. Sulfo-SANPAH is a long-arm (18.2 angstrom) crosslinker that contains an amine-reactive N-hydroxysuccinimide (NHS) ester and a photoactivatable nitrophenyl azide, also called sulfosuccinimidyl 6-(4'-azido-2'-nitrophenylamino)hexanoate. SDA (NHS-Diazirine) combines proven NHS-ester and diazirine-based photoreaction chemistries with conjugate amine-containing molecules with nearly any other functional group via long-wave UV-light activation. SDA (Sulfo-NHS-Diazirine) is an amine and photoreactive, membrane impermeable, heterobifunctional crosslinker with a 3.9 Angstrom spacer arm. Also called Sulfosuccinimidyl 4,4'-azipentanoate. LC-SDA (NHS-LC-Diazirine) is an amine and photoreactive, membrane permeable, heterobifunctional crosslinker with a 12.5 Angstrom spacer arm. Also called Succinimidyl 6-(4, 4'-azipentanamido)hexanoate. Sulfo-LC-SDA (Sulfo-NHS-LC-Diazirine) is a sulfo-NHS-diazirine based photoreactive crosslinker. Membrane impermeable with a 12.5 Angstrom spacer arm. Also called Sulfosuccinimidyl 6-(4,4'-azipentanamido)hexanoate.

a second filter that removes wavelengths above 370 nm could be beneficial but is not essential.

Calfskin type I collagen has been covalently attached to a polyacrylamide surface using sulfo-SANPAH. See Gaudet, C., "Influence of type I collagen surface density on Fibroblast Spreading, Motility, and Contractility" *Biophys J.* 85(5): 3329-3335 (2003). Collagen I was coupled to other surfaces using Sulfo-SANPAH in order to avoid potential differences in ECM remodeling on different substrates. See Trappman et al. "Extracellular-matrix tethering regulates stem-cell fate," *Nature Materials* (2012) (on-line publication). ROD has been covalently attached to a PDMS surface using sulfo-SANPAH. See Li et al., "RGD peptide-conjugated poly(dimethylsiloxane) promotes adhesion, proliferation, and collagen secretion of human fibroblasts," *J. Biomed Mat Res A.* 79(4):989-98 (2006).

It is not intended that the present invention be limited by the number or nature of channels in the microfluidic device. In some embodiments, the surface can be a surface of a fluid-flowing conduit or passageway disposed in a solid substrate. In some embodiments, the surface can be a solid surface. For example, in one embodiment, the solid surface can be a wall surface of a fluid channel, e.g., a microfluidic channel.

TABLE 1

Examples of commercially available crosslinkers

| Reactive Groups | Products | Spacer Arm (Å) | | Cleavable by? | Water-soluble? | Membrane permeable? |
|---|---|---|---|---|---|---|
| NHS ester/ aryl azide | ANB-NOS | 7.7 | Short | No | No | No |
| | Sulfo-SANPAH | 18.2 | Long | No | Yes | No |
| NHS ester/ diazirine | SDA | 3.9 | Short | No | No | Yes |
| | Sulfo-SDA | 3.9 | Short | No | Yes | No |
| | LC-SDA | 12.5 | Mid | No | No | Yes |
| | Sulfo-LC-SDA | 12.5 | Mid | No | Yes | No |
| | SDAD | 13.5 | Mid | Thiols | No | Yes |
| | Sulfo-SDAD | 13.5 | Mid | Thiols | Yes | No |

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—NH2) in pH 7-9 buffers to form stable amide bonds. The reaction results in the release of N-hydroxysuccinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using In one embodiment, the present invention contemplates a co-culture of liver sinusoidal endothelial cells in one chamber with hepatocytes in other chamber(s) to establish hepatic function in vitro. In one embodiment, the chambers are first and second microchannels aligned (e.g., vertically) with each other with one or more membranes separating them from each other ("liver-on-a-chip"). The liver-on-a-chip devices have been developed and optimized based on the basic design of an organ-on-a-chip as described in the U.S. Pat. No. 8,647,861, and the International Patent App. No. PCT/US2014/071611, the contents of each of which are incorporated herein by reference in their entireties. In some aspects, the inventors have optimized the design of the liver-on-a chip devices and culture conditions to provide long-term hepatic culture with physiologically relevant hepatic function (e.g., albumin and/or urea secretion, and/or CYP 450 metabolic capacity) for different animal models, e.g., human, rats, and dogs.

In a preferred embodiment, the present invention contemplates a microfluidic device comprising a microchannel, said microchannel comprising a monolayer of viable hepatocytes adhered to a coating, said coating comprising at least one extracellular matrix protein covalently coupled to a microchannel surface. The viable hepatocytes can be derived from different mammalian sources, including, e.g., but not limited to humans, rats, mice, and dogs.

In one embodiment, the present invention contemplates covalently attaching one or more proteins or peptides to a surface in the microfluidic device (e.g. to the membrane and/or one or more microchannel), and storing the microfluidic device for a week or more (a month or more) prior to attaching cells. In one embodiment, the present invention contemplates dry storage.

Experimental results have shown that chips for liver samples may be stored dry. That is to say, the extracellular matrix protein can be attached to the chip and can be stored dry (prior to any cell culture). However, not all ECM proteins can be stored dry; empirically, it was found that only some ECMs can be stored dry (collagens, fibronectin (FN)). Chips were stored at 4° C. and then compared to freshly coated chips.

FIG. 7A-C are photographs showing examples of liver cells (hepatic cells) on ECM coated chips under various conditions. Chips were coated with collagen I and fibronectin and stored either dry or wet for one week. Cells were then added to the chips and cultured for 14 days. As a control, a chip was coated fresh (no storage) and cultured with cells for 14 days. No differences in cell attachment were observed in Liver sinusoidal endothelial cells (LSECs) or Hepatic cells (Hep). No differences in morphology were observed (LSEC and Hep). FIG. 7A is the control (fresh ECM coat) after 14 days of cell culture. FIG. 7B shows the results after 1 week wet storage and cell culture for 14 days. FIG. 7C shows the results after 1 week dry storage and cell culture for 14 days.

Figure 8B:
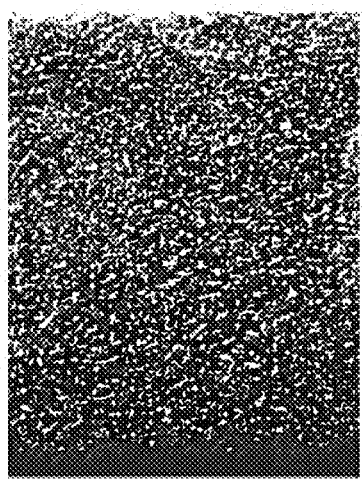
FIGS. 8A&B are photographs showing the results from a one month storage study. Chips were coated with collagen I and fibronectin and stored dry for one month. Liver cells were then added to the chips and cultured for 13 days (FIG. 8B). As a control, a chip was coated fresh (no storage) and cultured with cells for 13 days (FIG. 8A). No differences in cell attachment were observed (LSEC and Hep). No differences in morphology were observed (LSEC and Hep)
Figure 8A:
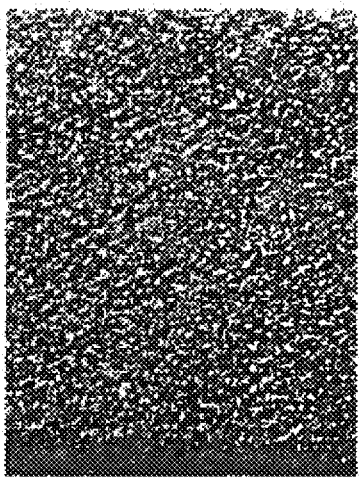

FIGS. 8A&B are photographs showing the results from a one month storage study. Chips were coated with collagen I and fibronectin and stored dry for one month. Liver cells were then added to the chips and cultured for 13 days (FIG. 8B). As a control, a chip was coated fresh (no storage) and cultured with cells for 13 days (FIG. 8A). No differences in cell attachment were observed (LSEC and Hep). No differences in morphology were observed (LSEC and Hep).

Figure 9A:
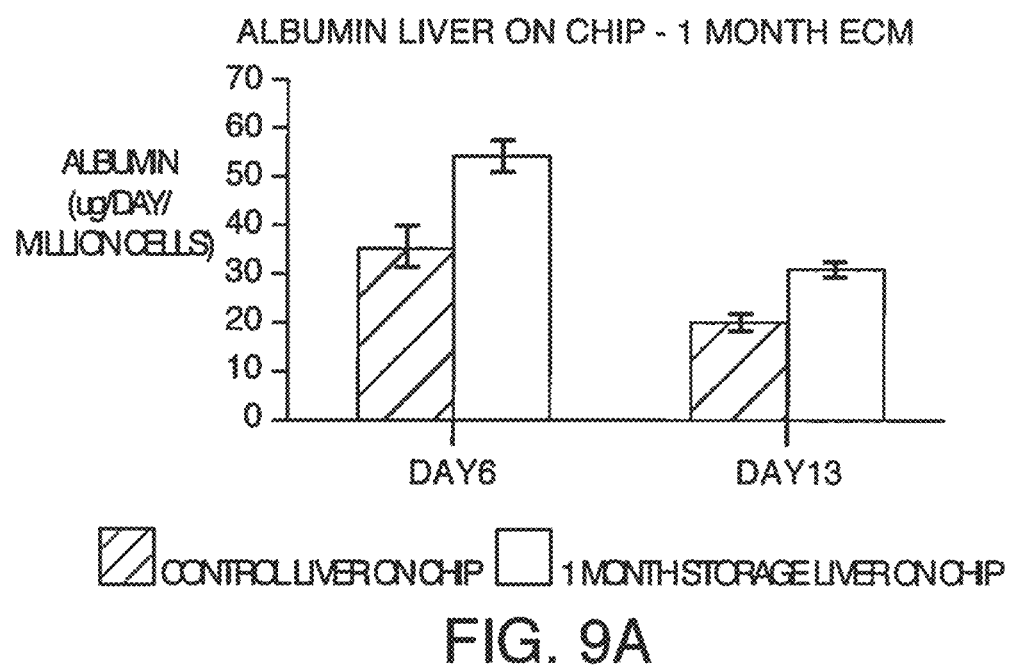
FIGS. 9A&B are bar graphs showing comparisons of different liver on chip examples. Chips were coated with collagen I and fibronectin and stored dry for one month. Liver cells (Hepatocytes) were then added to the chips and cultured (grey bars). As a control, a chip was coated fresh (no storage) and cultured with cells (blue bars). Albumin was measured in the culture fluid after 6 and 13 days of culture (FIG. 9A). LDH was measured in the culture fluid after 6 and 13 days (FIG. 9B).
Figure 9B:
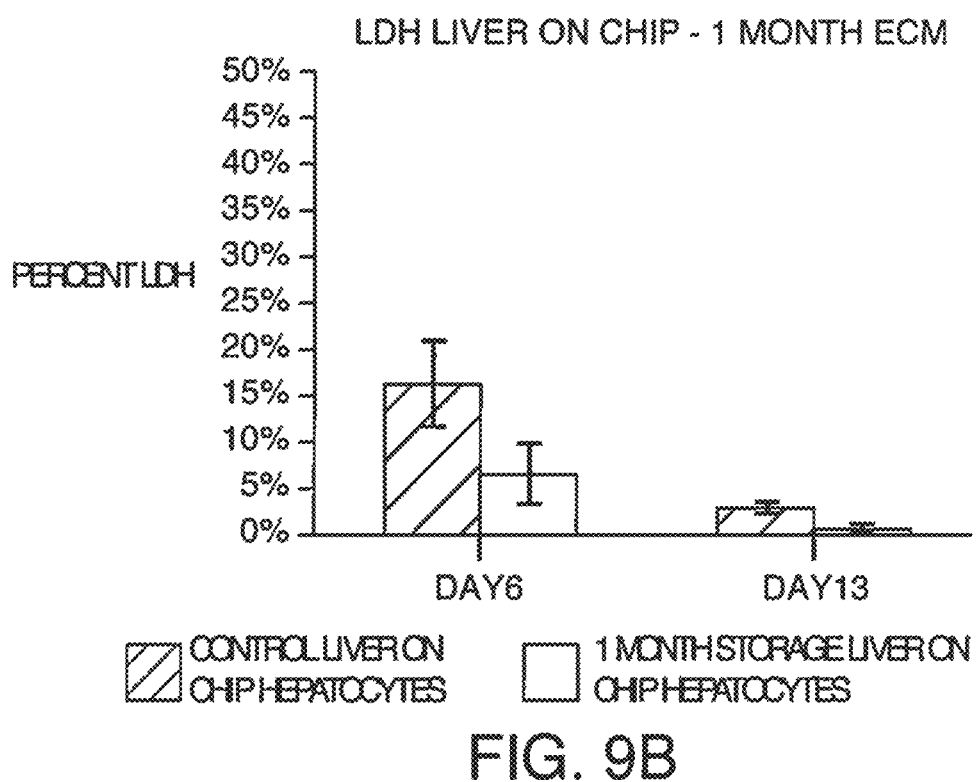

There was also an evaluation of biomarkers in order to compare between freshly coated (control) chips and chips dry-stored for 1 month with 5 chips tested per condition with liver. FIGS. 9A&B are bar graphs showing comparisons of different liver on chip examples. Chips were coated with collagen I and fibronectin and stored dry for one month. Liver cells (Hepaptocytes) were then added to the chips and cultured (second bars). As a control, a chip was coated fresh (no storage) and cultured with cells (first bars). Albumin was measured in the culture fluid after 6 and 13 days of culture (FIG. 9A). LDH was measured in the culture fluid after 6 and 13 days (FIG. 9B). Chips stored dry for 1 month showed higher albumin production and lower LHD release over a 2-week observation period. The LDH release is not desirable. Therefore, dry storage of col1/FN-coated chips is a viable platform for use with the human Liver-on-Chip.

The above results indicate that ECMs for Liver-on-Chip can be stored dry. Chips can be coated with collagen I and Fibronectin and put in a 1 week dry storage, and even a 1 month dry storage.

In one embodiment, the present invention contemplates covalently attaching one or more proteins or peptides to a surface in the microfluidic device (e.g. to the membrane and/or one or more microchannel), and storing the microfluidic device for a week or more (a month or more) prior to attaching cells. In one embodiment, the present invention contemplates wet storage. In one embodiment, the present invention contemplates vapor proof packaging.

In one embodiment, the present invention contemplates a membrane comprising a pattern. In one embodiment, the pattern is a line and groove pattern. Although it is not necessary to understand the mechanism of an invention, it is believed that a line and groove pattern provides alignment for cells such as muscle cells. It is further believed that it is microgrooves on the surface of the membrane that guides such cell alignment. In one embodiment, the membrane is a PDMS membrane.

In a preliminary experiment, PDMS membrane grooves were made using an existing micropatterned silicon wafer (e.g., 10 µm×10 µm×2 µm) as a mold. In one embodiment, a bifunctional crosslinker is attached to the micropatterned membrane. In one embodiment, the micropatterned membrane is in the flow channel of a microfluidic device. In one embodiment, the micropattern is parallel to the fluid flow. In one embodiment, the micropattern is perpendicular to the fluid flow. In one embodiment, an extracellular matrix protein (e.g. laminin) is attached to the crosslinker (e.g. covalently bound) so as to provide an ECM-coated micropatterned membrane. Human primary muscle cells were then cultured on the micropatterned PDMS membrane in a static culture condition. Cell alignment was measured by F-actin stain and image analysis. When micropatterned membranes were fabricated according to the methods described herein, cell alignment measurements demonstrated cell elongation. See, FIGS. 17A-D and FIG. 18.

In one embodiment, the PDMS membrane or micropatterned membrane may be selectively coated with a crosslinker using a mask. In one embodiment, the present invention contemplates the crosslinker used is Sulfo-SANPAH and the masking is done to control surface coating of this light activated crosslinker in a closed chip system (i.e. UV light can be used without opening the chip). For example, Sulfo-SANPAH may be applied via channels and ultraviolet light can be shined over the chip with a mask (to block the light from striking a specific portion or portions of the chip) covering a portion of an area, or alternatively a patterned mask to create a surface pattern. In one embodiment, the mask is layered, deposited or simply positioned on top of a portion of the membrane and subsequently exposed to UV light. Once the mask is removed, an ECM protein (or proteins) can be attached to the bifunctional crosslinker. In one embodiment, the irradiated membrane is washed before the ECM attachment step. Thereafter, cells may be attached to the resultant pattern generated by the mask and cultured in a static condition. Although it is not necessary to understand the mechanism of an invention, it is believed that most cells attach to ultraviolet light-exposed membrane areas (where the crosslinker was activated to bind) and very few cells attach in the masked areas (i.e., where there was no ultraviolet light exposure).

In one embodiment, the membrane micropatterning may be achieved by embossing. A preliminary experiment was performed using a pre-manufactured thin membrane layered on top of a conventional micropatterned silicon wafer which was then exposed to a high heat (e.g., about 80-90° C.) and a weight (to create pressure) for 24-48 hrs to create the embossed pattern. Subsequent to the embossing, the micropatterned membrane was removed from the silicon wafer. In one embodiment, the micropatterned membrane comprises PDMS. In one embodiment, the micropatterned membrane is in the flow channel of a microfluidic device. In one embodiment, the micropattern is parallel to the fluid flow. In one embodiment, the micropattern is perpendicular to the fluid flow. In one embodiment, a bifunctional crosslinker is attached to the micropatterned membrane. In one embodiment, an extracellular matrix protein (e.g. laminin) is attached to the crosslinker (e.g. covalently bound) so as to provide an ECM-coated micropatterned membrane. In one embodiment, the viable cells are further seeded onto the ECM-coated micropatterned membrane. In one embodiment, human primary muscle cells were attached to the membrane and cultured in a static condition. The data showed that the hSKMCs were bound to the membrane and observed to grow along the micropatterned grooves. After approximately six days of culture the hSKMCs were aligned along the microgrooves.

EXPERIMENTAL

The following are examples that further illustrate embodiments contemplated by the present invention. It is not intended that these examples provide any limitations on the present invention.

Example 1

Cellular Crosslinking to Improve Cell Attachment to Channels

In one embodiment, the present invention contemplates using a crosslinker to covalently attach proteins or peptides that enhance cell attachment. In this example, a protocol for using Sulfo-SANPAH as the crosslinker is provided as one embodiment of a method.

First, fresh 0.5 mM Sulfo-SANPAH (492.4 g/mol) solution in 50 mM HEPES (0.22 um sterile filtered, pH 7.4) (protect from light) is prepared. Then, an ECM solution is prepared (e.g. 50 ug/mL Laminin in PBS or media without FBS) on ice.

The microfluidic device ("chip") comprising a microchannel is then plasma treated. Plasma—15 sccm $O_2$, 60 sec, 100 W.

The channels are then washed with 200 uL of 50 mM HEPES. Excess 50 mM HEPES is removed from the channel.

Sulfo-SANPAH is introduced into the microchannel by inserting a pipet tip reservoir in a port of the chip. 100 uL of Sulfo-SANPAH solution is added to the top channel, ejecting tip into inlet port. 50 uL of Sulfo-SANPAH solution is added to the bottom channel, ejecting tip into inlet port. The channels are then inspected to be sure no bubbles are present. At this point, one carefully removes and discards the pipet tips reservoirs without spilling excess reagent on surface of chip.

At this point, the chips are ready for light treatment. The chips are incubated in the UV lamp chamber. Decrease distance to UV lamp and chips with 1 mL tip boxes or lab-jack. The incubation is for 20 min at 0.72 joules/cm². After UV treatment, Sulfo-SANPAH is removed from the channels and each channel is washed twice with 200 uL 50 mM HEPES. The channel is dried by removing or aspirating remaining HEPES buffer.

At this point, a protein or peptide can be attached. A solution containing a protein (e.g. ECM solution) or peptide (to enhance cell binding) can be loaded into the channels with one of the following conditions: Overnight at 4° C. or Minimum of 1.5 hours at 37° C.

Before seeding with cells, the solution (e.g. ECM solution) should be removed from the channels and the channels washed with 200 uL of desired media or PBS.

Example 2

Channel Surface Modification to Improve Cell Attachment

Figure 3A:
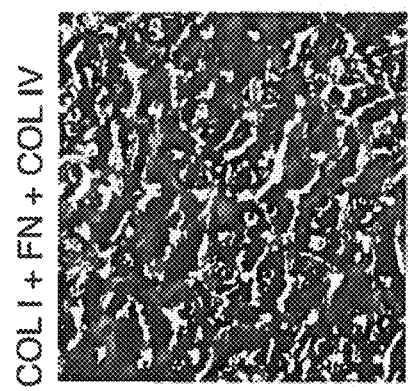
FIG. 3A-D show photographs of hepatocytes six (6) days after being seeded on a PDMS surface that was either plasma treated (FIGS. 3 A & B) or that was Sulfo-SANPAH treated (i.e. ECM protein(s) covalently attached to the surface with this crosslinker) (FIGS. 3 C & D). The cells were cultured under flow conditions for two (2) days.
Figure 3B:
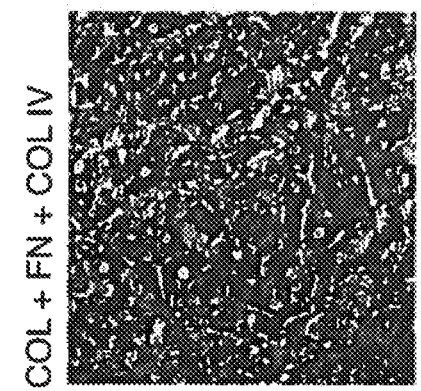
Figure 3C:
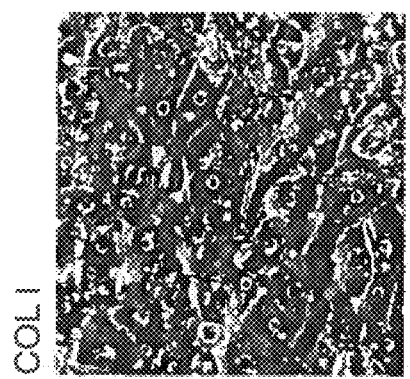
Figure 3D:
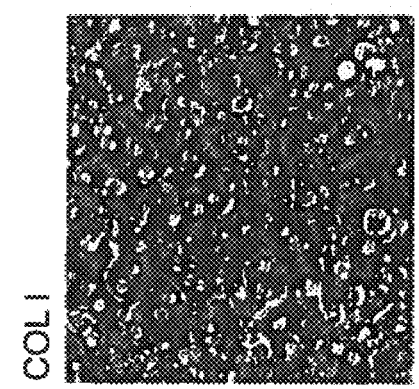

In this example, PDMS surfaces treated with plasma were compared with PDMS surfaces modified by covalent attachment ECM proteins. FIGS. 3A-B show photographs of hepatocytes six (6) days after being seeded on a PDMS surface that was either plasma treated (FIGS. 3 A & B) or that was Sulfo-SANPAH treated (i.e. ECM protein(s) covalently attached to the surface with this crosslinker) (FIGS. 3 C & D). The cells were cultured under flow conditions for two (2) days.

Figure 4A:
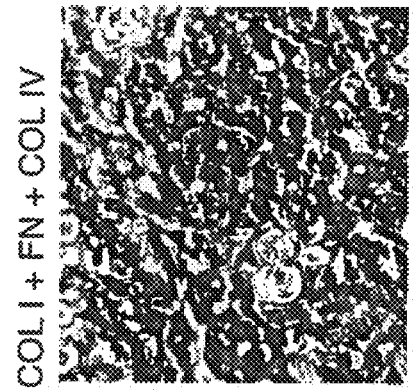
FIG. 4A-D show photographs of hepatocytes nine (9) days after being seeded on a PDMS surface that was either plasma treated (FIGS. 4A & B) or that was Sulfo-SANPAH treated (i.e. ECM protein(s) covalently attached to the surface with this crosslinker) (FIGS. 4C & D). The cells were cultured under flow conditions for 5 days.
Figure 4B:
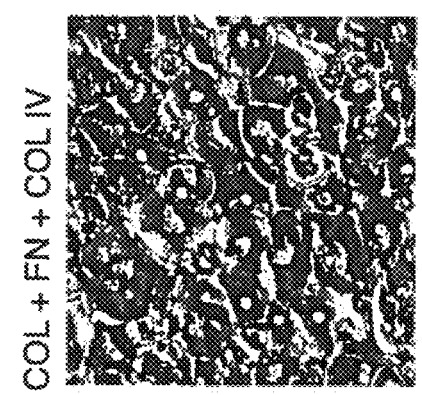
Figure 4C:
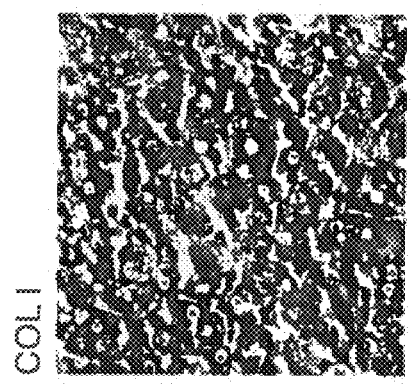
Figure 4D:
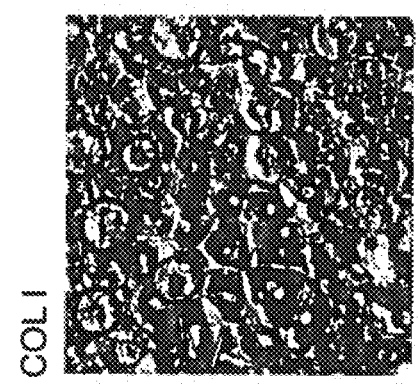

FIGS. 4A-D show photographs of hepatocytes nine (9) days after being seeded on a PDMS surface that was either plasma treated (FIGS. 4A & B) or that was Sulfo-SANPAH treated (i.e. ECM protein(s) covalently attached to the surface with this crosslinker) (FIGS. 4C & D). The cells were cultured under flow conditions for 5 days.

Figure 5A:
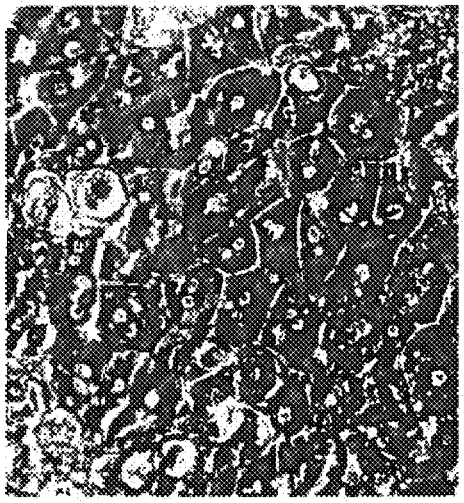
FIGS. 5 A&B show photographs of hepatocytes fourteen (14) days after being seeded on a PDMS surface that was either plasma treated (FIG. 5A) or that was Sulfo-SANPAH treated (i.e. ECM protein(s) covalently attached to the surface with this crosslinker) (FIG. 5B). The cells were cultured under flow conditions for 10 days. ECM: Collagen type I 100 ug/ml+FN 50 ug/ml+Collagen type IV 50 ug/ml. Cells on the Sulfo-SANPAH treated surface (right) maintained monolayer over 14 days in culture. Cells on the plasma treated surface (left) started to detach (see arrow).
Figure 5B:
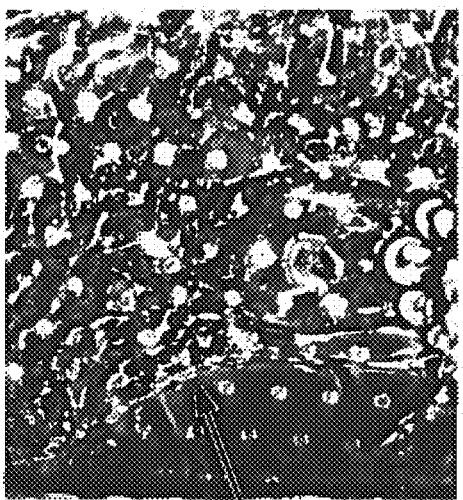
Figure 6:
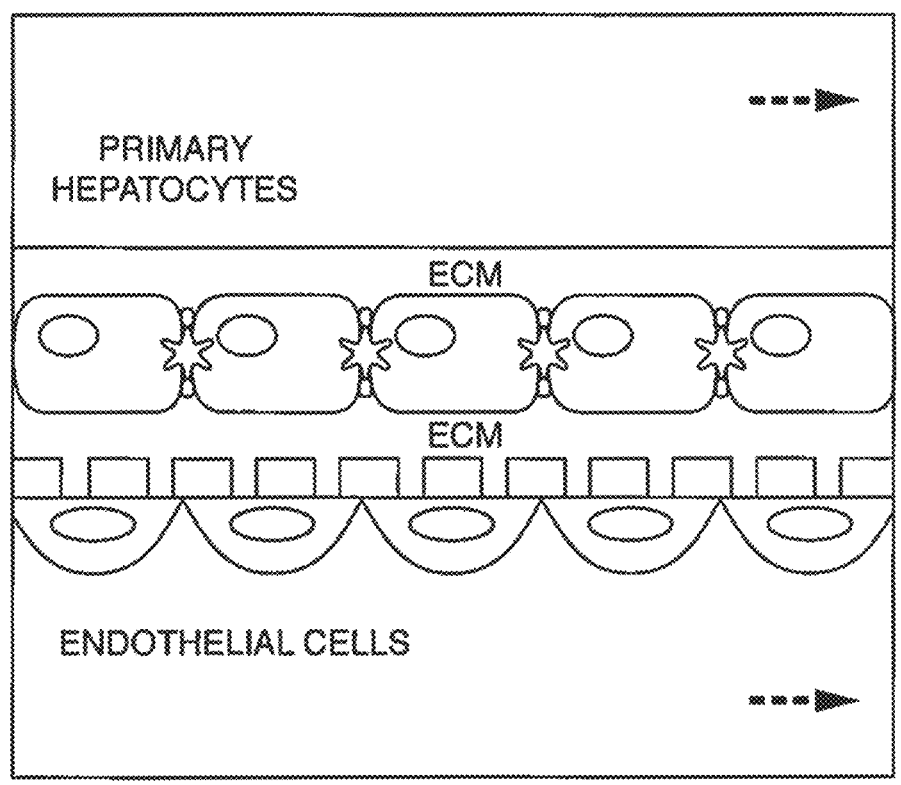
FIG. 6 is a drawing showing the extracellular matrix (ECM) next to primary hepatocytes and endothelial cells.

FIGS. 5A-B show photographs of hepatocytes fourteen (14) days after being seeded on a PDMS surface that was either plasma treated (FIG. 5A) or that was Sulfo-SANPAH treated (i.e. ECM protein(s) covalently attached to the surface with this crosslinker) (FIG. 5B). The cells were cultured under flow conditions for 10 days. ECM: Collagen type I 100 ug/ml+FN 50 ug/ml+Collagen type IV 50 ug/ml. Cells on the Sulfo-SANPAH treated surface (right) maintained monolayer over 14 days in culture. Cells on the plasma treated surface (left) started to detach (see arrow). Clearly, the Sulfo-SANPAH treatment was an improvement over plasma treatment.

Example 3

Shelf-Life Study of ECM-Coated Chips

This example evaluates conditions to avoid ECM (i.e., for example, laminin, Matrigel) inactivation found during dry storage. All tested chips were stored at 4° C. then compared to freshly coated chips. Results indicate that ECM for Gut-on-Chip chips are best stored in solution (e.g., wet).
Experimental Design The ECM for Gut-on Chip chips comprised Matrigel and collagen 1. Gut-on-Chip chips were chosen as test platform due to its robustness to varying culture conditions. In particular, test Chips were treated with Sulfo-SANPAH and ECM (100 ug/mL Martigel and 25 ug/mL collagen I). All conditions were compared to freshly coated chips.
Results Twenty-eight (28 chips) were stored for 1 week. No differences in Caco-2 and HUVEC cell attachment was observed. No differences in Caco-2 and HUVEC cell morphology was observed. The chips were maintained for 8 days prior to exposure to TNF-α and IL-1β. The experiment also included some chips with lamina propria cells. Samples for barrier function and lactate dehydrogenase (LDH) were collected, along with cytokine profiles.

Figure 10A:
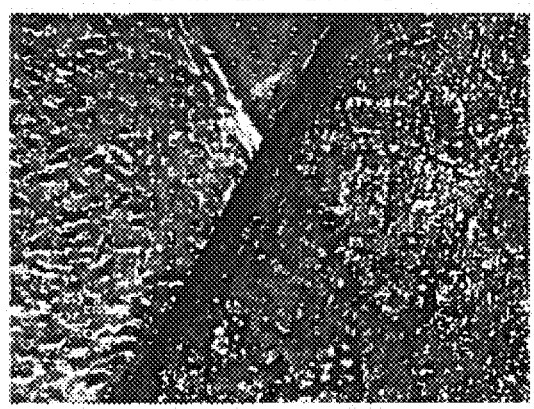
FIG. 10A-C are photographs showing the results from a 1 week gut-on-chip storage study. Chips were ECM coated (Matrigel and collagen I) and stored wet for 1 week. Thereafter, Human Umbilical Vein Endothelial Cells (HUVEC) and Caco-2 cells were cultured on the chip for 11 days. Caco-2 cells and HUVEC were on each chip with the Caco-2 cells are on the top side of the membrane and the HUVEC are on the bottom.
Figure 10B:
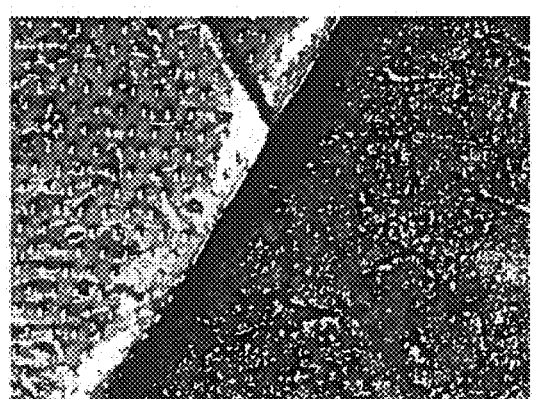
Figure 10C:
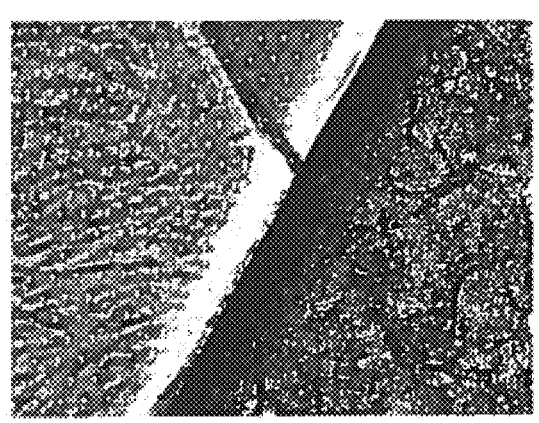
Figure 11A:
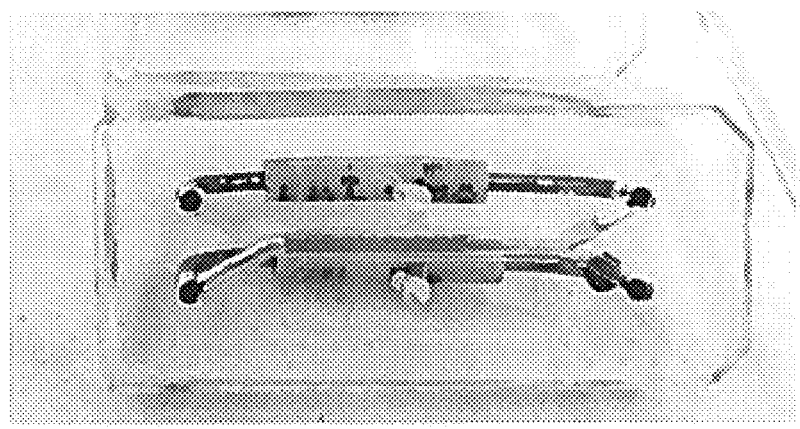
FIGS. 11A&B are photographs showing small amounts of air observed in bottom channel inlets after wet storage because PDMS is vapor permeable.
Figure 11B:
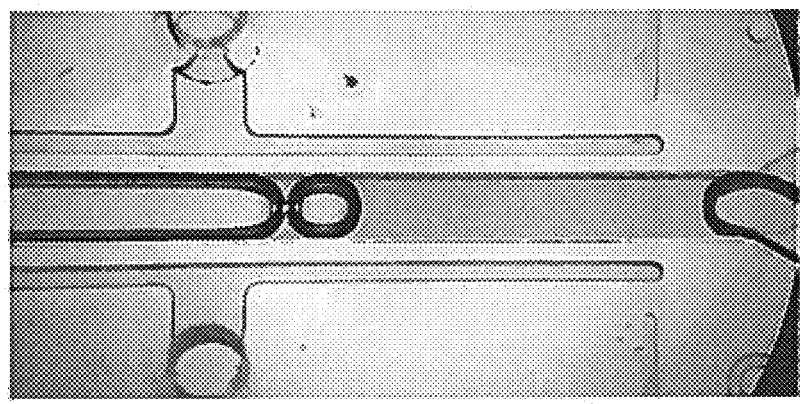
FIG. 11B shows a close up of air observed in the bottom channel inlets after wet storage for 4 weeks. Small amounts of air observed in bottom channel inlets after 12 days of storage. Air volume increased after 3 weeks (FIG. 11A). By 30 days, most ECM solution has evaporated from the chip.

It appears that a 1 week storage does not impact cell attachment or morphology in the Gut-on-Chip configuration. FIG. 10A-C show photographs demonstrating the results from a 1 week gut-on-chip storage study. Chips were ECM coated (Matrigel and collagen I) and stored wet for 1 week. Thereafter, Human Umbilical Vein Endothelial Cells (HUVEC) and Caco-2 cells were cultured on the chip for 11 days. Caco-2 cells and HUVEC were on each chip with the Caco-2 cells on the top side of the membrane and the HUVEC on the bottom side of the membrane. FIG. 10A-C show examples of gut on chips where the chips have been stored for 1 week. FIG. 10A-C images were taken at the point of the chip where the two channels join, the wall of the channel is the dark separator in the images. This is a top-down view. The gut function is assessed via barrier function (pApp, the system's permeability coefficient) and response to stimulation (using an inflammatory stimulus). The increasing barrier function (see FIG. 12) demonstrates healthy and functional cell populations and correlates with previous data. Caco-2 and HUVEC cells were used. Wet storage (1 week) of Matrigel/Col1 coated chips are a viable platform for use with the human Out-on-Chip.

Figure 12:
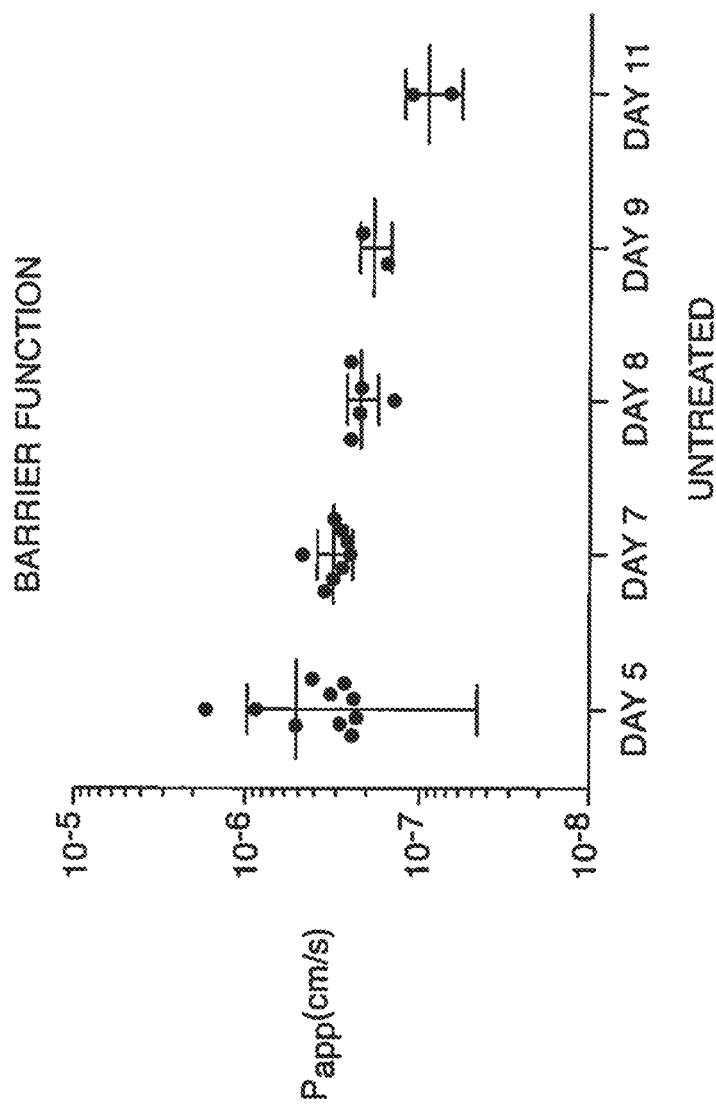
FIG. 12 is a graph showing the increasing barrier function of cells in the gut-on-chip. Chips were coated with Matrigel and collagen I and stored wet for one week. Thereafter, the gut cells (Caco-2 and HUVEC cells) were added to the chip and cultured. The results demonstrate healthy and functional cell populations.

FIG. 12 shows the increasing barrier function which demonstrates healthy and functional cell populations. The FIG. 12 graph shows the increasing barrier function of cells in the gut-on-chip. Chips were coated with Matrigel and collagen I and stored wet for one week. Thereafter, the gut cells (Caco-2 and HUVEC cells) were added to the chip and cultured. The results demonstrate healthy and functional cell populations.

In conclusion, the data shows that the storage of Out-on-Chip coated with extracellular protein should be stored wet, such that more than 1 week leads to evaporation issues. However, with a vapor proof packaging, the wet storage lifespan would be expected to improve.

The present invention contemplates other chips, such as those that use Laminin and/or Matrigel and may include chips that could be used as Intestine-on-Chip, Blood Brain Barrier (BBB)-on-Chip, and neruromuscular junction (NMJ)-on-Chip.

Example 4

Enhanced Cell Attachment in Presence of Crosslinker and Laminin

This example shows that the coating of a channel with crosslinker and laminin improves the binding of cells to chip channels. The experimental design coated chip channels with one of several concentrations (0.1 mg/ml, 0.5 mg/ml and 1 mg/ml) of Sulfo-SANPAH (IV), followed by one of several concentrations (10 μg/ml, 50 μg/ml and 100 μg/ml) of fluorescently labeled laminin (red).

In general the protocol was as follows:
1. Flush the chip with 70% ethanol briefly and wash with 50 mM HEPES buffer.
2. Add 50 μl of Sulfo-SANPAH (IV) and incubate under an ultraviolet light for approximately 20 min.
3. Wash with 200 μl of 50 mM HEPES buffer three (3) times.
4. Wash with 200 μl of DPBS twice.
5. Add 50 μl of Laminin and incubate at 4° C. overnight.
6. Next day, transfer the chip at 37° C. for at least 1 h.
7. Seed the chip with motor neuron cells and culture.

Data collected before seeding with motor neuron cells shows increased laminin binding as the laminin concentration increases. See, FIG. 13A-C. Data collected after seeding with motor neuron cells shows that the cells grown on higher concentrations of laminin were differentiated and developed thicker axons. See, FIGS. 14A&B.

Example 5

Micropatterning of a Chin Membrane

Figure 15A:
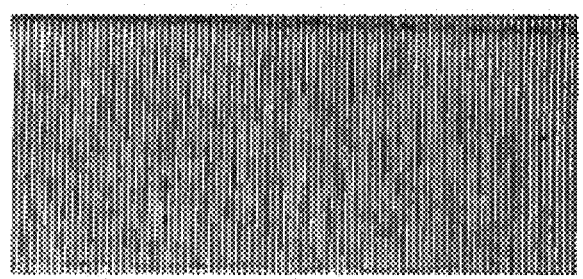
FIGS. 15A&B presents alternative embodiments of PDMS membrane micropatterning.
Figure 15B:
FIG. 15B: Micropatterning parallel to channel fluid flow.
Figure 16A:
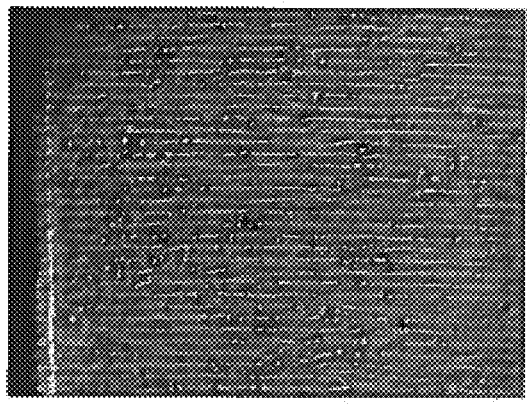
FIG. 16A-D presents exemplary data showing nuclei development within human skeletal muscle cell (hSKMC) myotubes.
Figure 16B:
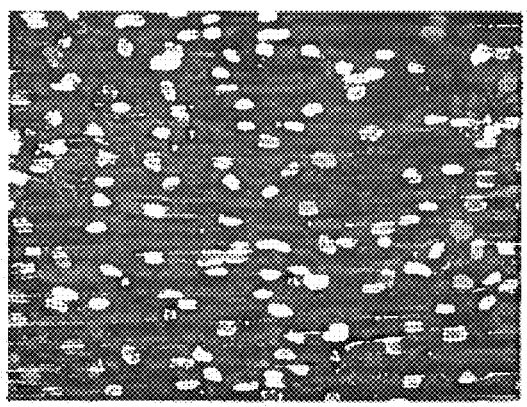
Figure 16C:
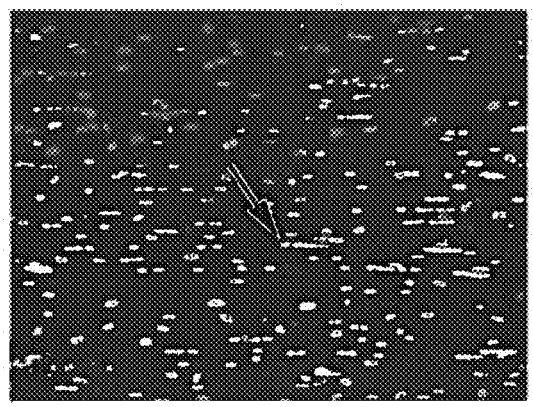
Figure 16D:
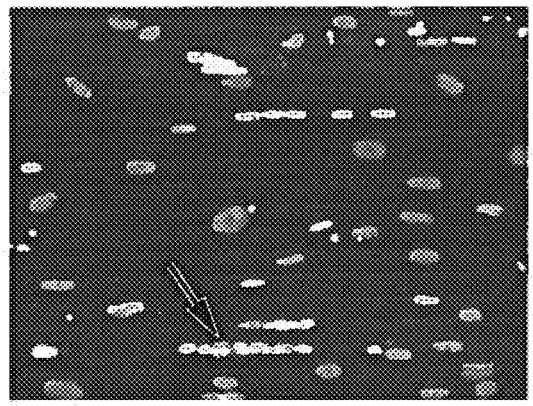
Figure 17A:
FIG. 17A-D presents exemplary data showing actin growth and development within human skeletal muscle cell (hSKMC) myotubes.
Figure 17B:
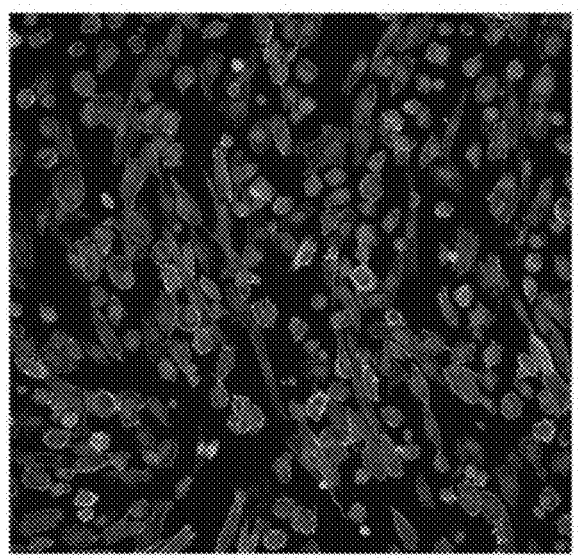
Figure 17C:
Figure 17D:
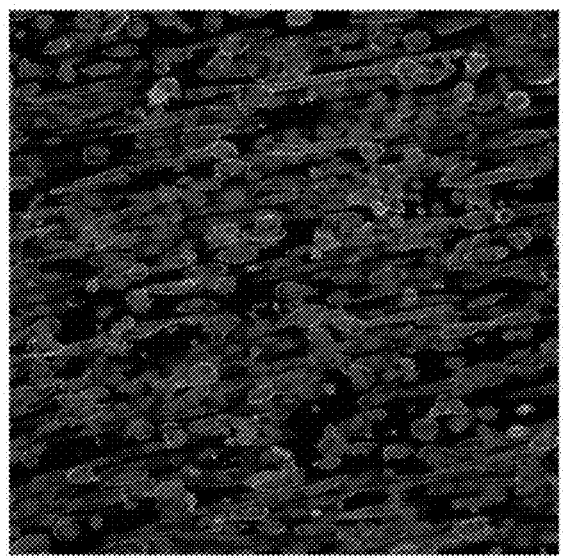
Figure 18:
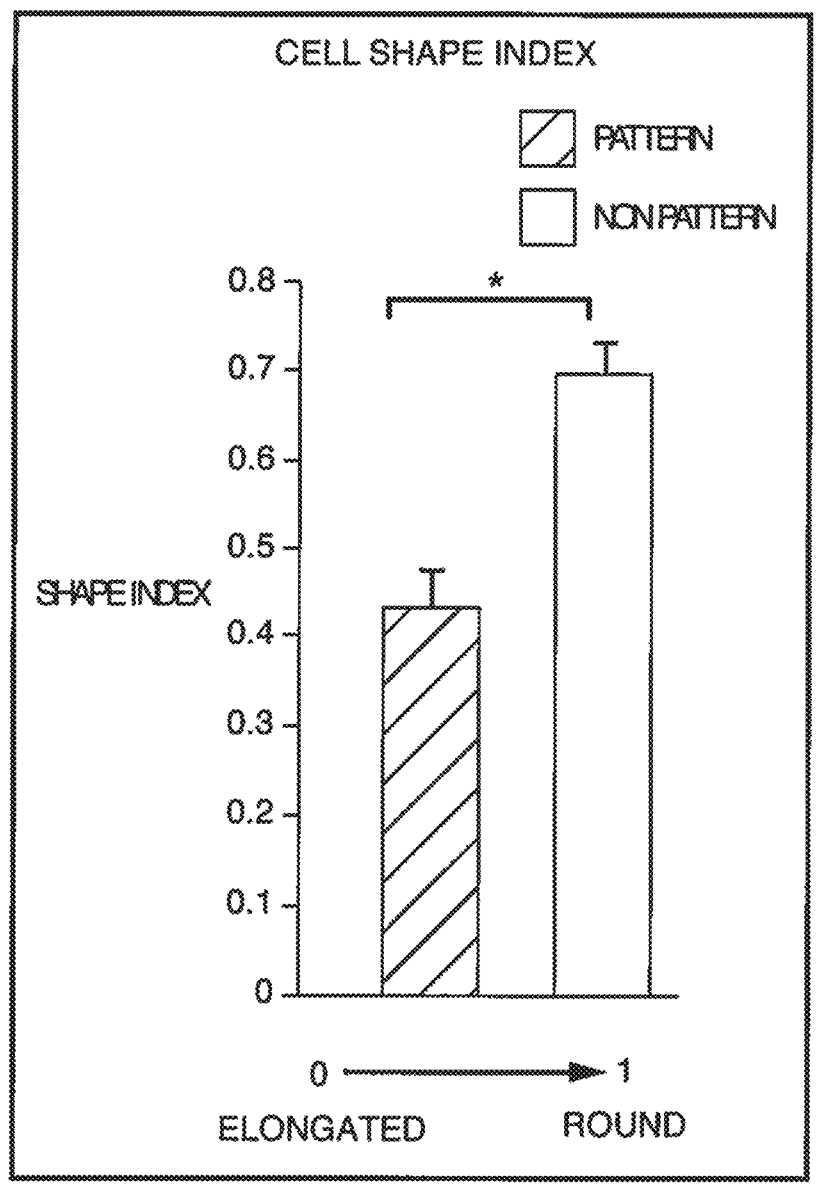
FIG. 18 presents exemplary data in a bar graph showing hSKMC morphology (e.g., elongated or round) as measured by a cell shape index.

This example shows one method of micropatterning a PDMS membrane to facilitate cell alignment in a chip. In general the protocol was as follows:
1. Prepare silicon wafer mold comprising 10×2 μm grooves.
2. Spin coat PDMS on top of the silicone mold.
3. Cure at 60° C. for over 6 hours.
4. Delaminate the micropatterned PDMS membrane from the silicon wafer mold and assemble the micropattern PDMS membrane into a channel chip in either a perpendicular or parallel orientation relative to fluid flow. See, FIG. 15A and FIG. 15B, respectively.
5. Surface treat with Sulfo-SANPAH and coat chips with Laminin.
6. Seed human skeletal muscle cells (hSKMC)
7. Subsequent to culturing, observe cell morphology and cell alignment relative to the micropatterning.
8. Stain for muscle markers to show viability, differentiation and development.
9. Assess the hSKMCs for spontaneous contraction, cholinergic stimulation and IHC The data show: i) hSKMC alignment within the PDMS groove micropattern (FIG. 16A); ii) progressive nuclei development within hSKMC myotubes between Day 3-Day 11 of culture (FIGS. 16B-C); iii) greater actin development within hSKMCs cultured on micropatterned membranes by Day 7 (FIGS. 17A-D); iv) greater proportion of elongated versus round hSKMC morphology by Day 7 (FIG. 18).

Example 6

Membrane Micropatterning Using a Mask

This example creates a membrane surface pattern using Sulfo-SANPH and a mask.

In general the protocol was as follows:
1. Sulfo-SANPAH (0.5 mg/ml) was added onto PDMS membrane.
2. A mask (e.g. a piece of aluminum foil) was overlayed on top of a portion of the PDMS membrane.
3. The membrane with mask was transferred under an ultraviolet light and illuminated for 20 min
4. The membrane was washed and Laminin was added and incubated for 2 h at 37° C. incubator
5. Next day, hSKMC cells were seeded on to the membrane
6. The seeded hSKMC cells were then cultured for 7 days.

Figure 19A:
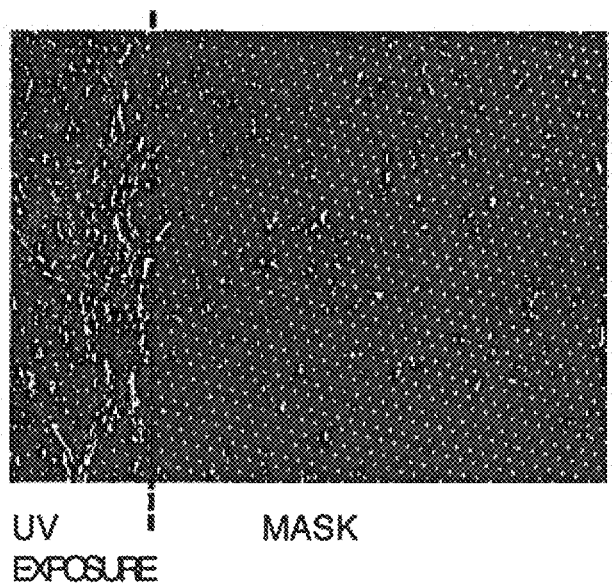
FIG. 19A and FIG. 19B show exemplary data showing greater hSKMC attachment to PDMS membranes in unmasked regions versus masked regions due to UV-activated crosslinkers.
Figure 19B:
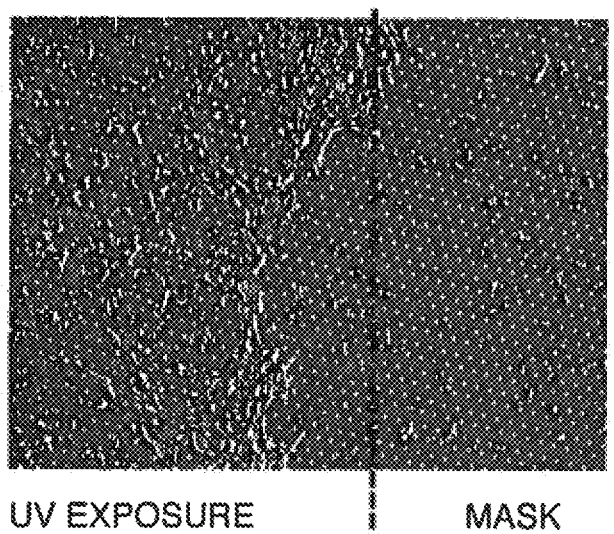

The data show that the regions where Sulfo-SANPAH was activated by exposure to ultraviolet light have greater sSKMC cell attachment than those masked regions (e.g., no Sulfo-SANPAH activation). See, FIGS. 19A&B.

Example 7

Membrane Micropatterning Using Embossing

Figure 20A:
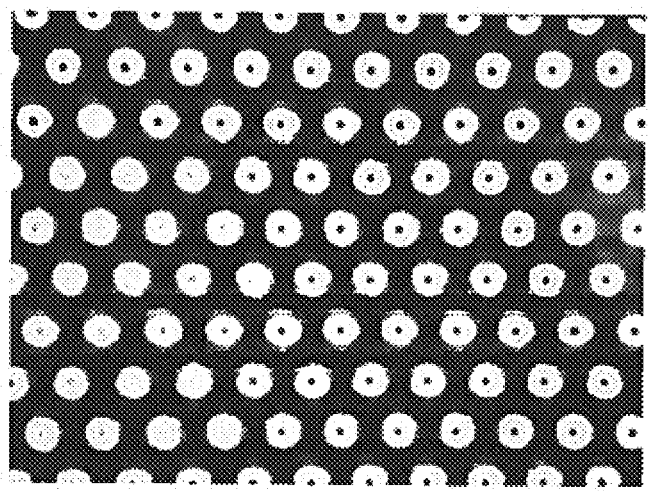
FIG. 20A-C presents exemplary data showing the fabrication and use of an embossed PDMS membrane.
Figure 20B:
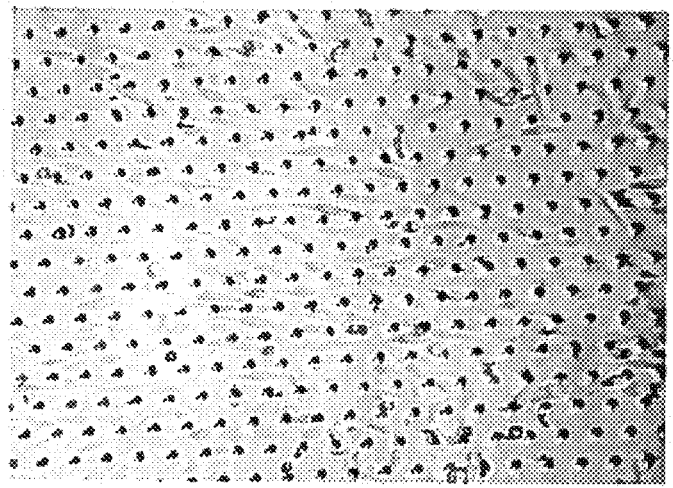
Figure 20C:
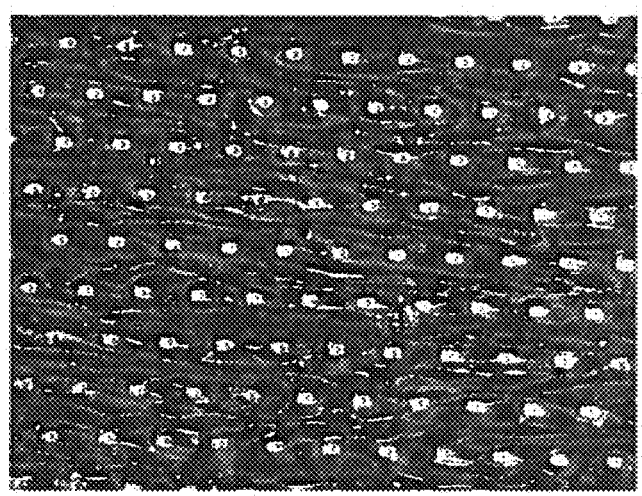
Figure 21:
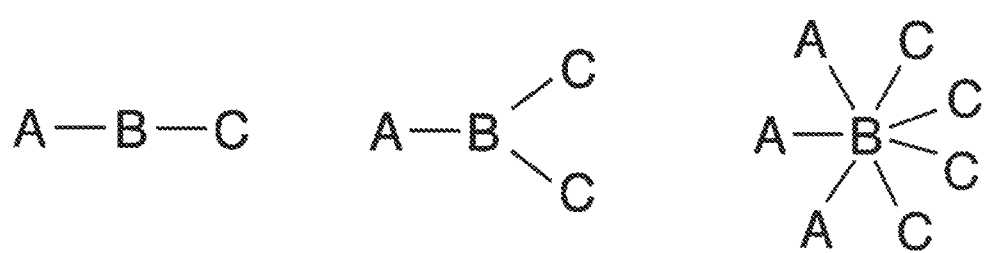
FIG. 21 shows generic examples of potential crosslinkers with the formula A-B-C, wherein A represents light-reactive portion, B represents a linker, and C represents modifier-reactive portion. The formula on the left represents a linear crosslinker, the formula in the center and the left represent where the linker portion is multivalent.
Figure 22:
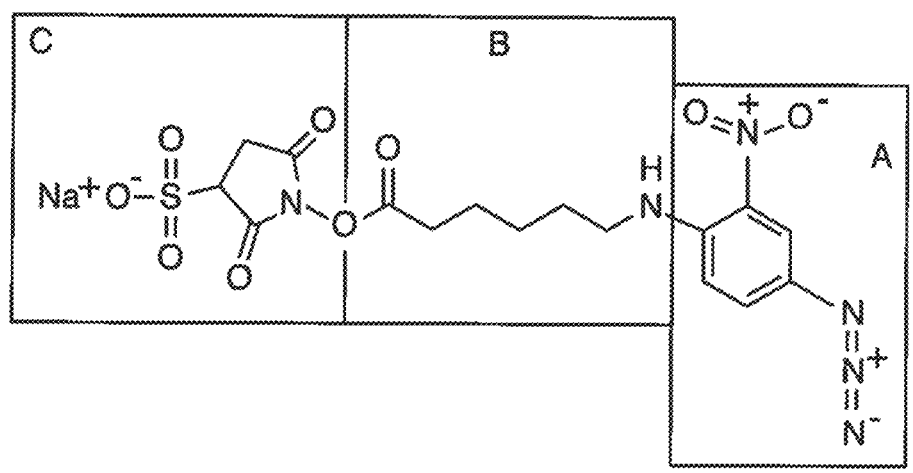
FIG. 22 shows a specific example of a crosslinker, Sulfo-SANPAH which is diagrammed according to the A-B-C crosslinker formula described above.

This example creates a membrane surface pattern using embossing with heat a pressure. In general the protocol was as follows:
1. A PDMS membrane was embossed onto silicon wafer at 80° C. for 2 days with pressure.
2. At day 2, the embossed PDMS membrane was delaminated from the wafer.
3. Sulfo-SANPAH (0.5 mg/ml) was added onto PDMS membrane and treated under ultraviolet light for 20 min.
4. The irradiated membrane was washed and Laminin was added and incubated for 2 h at 37° C.
5. Next day, hSKMC cells were seeded onto the membrane.
6. The seeded hSKMC cells were then cultured for 7 days A representative embossed PDMS membrane patterns is shown in FIG. 20A. The growth of hSKMC cells was observed on the embossed PDMS membrane patterns after Day 1 and Day 6 of culture. See, FIG. 20B and FIG. 20C, respectively.

While embodiments and applications have been shown and described, it would be apparent to those skilled in the art having the benefit of this disclosure that many more modifications than mentioned above are possible without departing from the inventive concepts disclosed herein. It is specifically contemplated that some of the features described above can be combined. For example, the membrane can be micropatterned to create a first pattern (e.g. by molding or embossing features such as lines, grooves, etc.) and then a crosslinker can be used with a mask to create a second pattern. The embodiment(s), therefore, are not to be restricted except in the spirit of the appended claims.

We claim:

1. A method of treating a microfluidic device, comprising:
   a) providing:
      i) a microfluidic device comprising a microchannel comprising a plasma treated polydimethylsiloxane surface;
      ii) a fluidic source comprising a fluid, wherein said fluidic source is in fluidic communication with said microchannel; and
      iii) a source of ultraviolent light and an N-sulphosuccinimidyl-6-(4'-azido-2'-nitrophenylamino) hexanoate heterobifunctional crosslinker having an ultraviolet light reactive portion and a chemically reactive portion;
   b) exposing said ultraviolet light reactive portion of said N-sulphosuccinimidyl-6-(4'-azido-2'-nitrophenylamino) hexanoate heterobifunctional crosslinker to said source thereby covalently attaching said crosslinker to said surface;
   c) covalently attaching laminin with said chemically reactive portion of said crosslinker so as to create a laminin-treated surface;
   d) storing said microfluidic device comprising the laminin-treated surface in a solution, wherein said storing is done at a controlled temperature below room temperature;
   e) removing said microfluidic device from said storing;
   f) seeding viable epithelial cells on said laminin-treated surface so as to create attached epithelial cells;
   g) flowing said fluid from said fluid source through said microchannel so as to create flow conditions; and
   h) culturing said attached epithelial cells under said flow conditions such that said attached epithelial cells remain attached and viable for at least 7 days.

2. The method of claim 1, wherein said storing is done at between 2 and 10° C.

3. A method for culturing cells, comprising:
   a) providing;
      i) a microfluidic device comprising a microchannel comprising a membrane with a polydimethylsiloxane surface;
      ii) a fluidic source comprising a fluid, wherein said fluidic source is in fluidic communication with said microchannel; and
      iii) a source of ultraviolent light;
   b) exposing an ultraviolet light reactive portion of an N-sulphosuccinimidyl-6-(4'-azido-2'-nitrophenylamino) hexanoate crosslinker to said source thereby covalently attaching said crosslinker to said surface;
   c) covalently attaching an extracellular matrix protein with a chemically reactive portion of said crosslinker so as to create a treated surface,
   d) seeding viable epithelial cells on said protein so as to create attached epithelial cells;
   e) flowing fluid in a parallel orientation to said membrane so as to create flowing conditions; and
   f) culturing said attached epithelial cells that remain attached and viable for at least 14 days under said flow conditions.

4. The method of claim 3, wherein said viable epithelial cells are hepatocytes.

5. A method of culturing cells, comprising:
   a) providing:
      i) a microfluidic device comprising a microchannel comprising a plasma treated polydimethylsiloxane surface;
      ii) a fluid source comprising a fluid in fluidic communication with said microchannel; and
      iii) a source of ultraviolet light and an N-sulphosuccinimidyl-6-(4'-azido-2'-nitrophenylamino) hexanoate crosslinker having an ultraviolet light reactive portion and a chemically reactive portion;
   b) exposing said ultraviolet light reactive portion of said N-sulphosuccinimidyl-6-(4'-azido-2'-nitrophenylamino) hexanoate crosslinker to said source thereby covalently attaching said crosslinker to said surface;
   c) covalently attaching one or more extracellular matrix proteins to said chemically reactive portion of said attached crosslinker as to create a treated surface;
   d) seeding viable epithelial cells on said treated surface so as to create attached epithelial cells;
   e) flowing said fluid from said fluid source through said microchannel so as to create flowing conditions; and
   f) culturing said attached epithelial cells that remain attached and viable under said flow conditions for at least 7 days.

6. The method of claim 5, wherein said surface is a membrane.

7. The method of claim 5, wherein said light reactive portion of said crosslinker is activated with an ultraviolet light in the presence of a mask.

* * * * *